(12) United States Patent
Yan et al.

(10) Patent No.: US 6,900,040 B2
(45) Date of Patent: May 31, 2005

(54) ISOLATED HUMAN DEHYDROGENASEPROTEINS, NUCLEIC ACID MOLECULES ENCODING THESE HUMAN DEHYDROGENASE PROTEINS, AND USES THEREOF

(75) Inventors: Chunhua Yan, Boyds, MD (US); Zhenya Li, Boyds, MD (US); Gennady V Merkulov, Baltimore, MD (US); Valentina Di Francesco, Rockville, MD (US); Ellen Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 31 days.

(21) Appl. No.: 10/359,076

(22) Filed: Feb. 6, 2003

(65) Prior Publication Data

US 2003/0138930 A1 Jul. 24, 2003

Related U.S. Application Data

(60) Division of application No. 09/876,216, filed on Jun. 8, 2001, now Pat. No. 6,544,764, which is a continuation-in-part of application No. 09/805,457, filed on Mar. 14, 2001, now abandoned.

(60) Provisional application No. 60/247,922, filed on Nov. 14, 2000.

(51) Int. Cl.$^7$ .............................. C12N 9/04; C07H 21/04

(52) U.S. Cl. ....................................... 435/190; 536/23.2

(58) Field of Search ........................... 435/190; 536/23.2

*Primary Examiner*—Ponnathapu Achutamurthy
*Assistant Examiner*—Yong D. Pak
(74) *Attorney, Agent, or Firm*—Celera Genomics; Lin Sun-Hoffman

(57) ABSTRACT

The present invention provides amino acid sequences of polypeptides that are encoded by genes within the human genome, the dehydrogenase polypeptides of the present invention. The present invention specifically provides isolated polypeptide and nucleic acid molecules, methods of identifying orthologs and paralogs of the dehydrogenase polypeptides, and methods of identifying modulators of the dehydrogenase polypeptides.

4 Claims, 12 Drawing Sheets

```
  1 TTGGCCATCA CATTCCCCTT GCCCTATGGC GGCCCTCACA GACCTCTCAT
 51 TTATGTATCG CTGGTTCAAG AACTGCAATC TGGTTGGCAG CCTCTCAGAG
101 AAGTACGTCT TCATCACAGG CTGTGACTCT GGCTTCGGGA ACCTGCTGGC
151 CAAACAGCTG GTTGATCGGG GCATGCAGGT GCTGGCTGCT TGCTTCACTG
201 AGGAGGGATC CCAGAAACTT CAGCGGGATA CCTCCTATCG GCTGCAGACC
251 ACCCTACTGG ATGTCACCAA GAGCGAAAGC ATCAAGGCGG CGGCCCAGTG
301 GGTGAGGGAC AAAGTGGGCG AACAAGGCCT CTGGGCCCTG GTGAACAATG
351 CTGGTGTGGG CCTGCCCAGT GGTCCCAACG AATGGCTGAC CAAGGATGAC
401 TTTGTGAAGG TGATTAATGT GAACCTGGTG GGACTGATCG AAGTGACCCT
451 TCACATGCTG CCCATGGTCA AGAGAGCCCG GGGCAGGGTT GTCAACATGT
501 CCAGCTCTGG TGGTCGTGTG GCTGTCATTG GTGGTGGCTA CTGCGTCTCC
551 AAGTTTGGCG TTGAGGCCTT CTCTGACAGC ATAAGGCGTG AGCTCTACTA
601 CTTTGGGGTG AAAGTCTGCA TCATTGAGCC AGGGAACTAT CGGACAGCCA
651 TTCTCGGCAA GGAGAACCTG GAGTCACGCA TGCGAAAGCT TTGGGAGAGG
701 CTGCCTCAGG AGACCCGGGA CAGCTACGGA GAGGATTATT TCCGCGTCTA
751 TACTGACAAG TTAAAAAACA TAATGCAGGT GGCAGAGCCC AGAGTCAGAG
801 ATGTCATCAA CAGCATGGAG CATGCTATTG TTTCCCGGAG CCCTCGCATC
851 CGCTACAACC CTGGCCTGGA TGCCAAACTC CTCTACATCC CTCTGGCTAA
901 GTTGCCCACC CCTGTGACAG ATTTCATCCT AAGCCGGTAC CTTCCAAGGC
951 CAGCGGACAG TGTCTAAACT GGGGAGGATC AATGGGTCAG TGG  (SEQ ID NO:1)
```

FEATURES:
5'UTR:       1-25
Start Codon: 26
Stop Codon:  965
3'UTR:       968

```
  1 TTGGCCATCA CATTCCCCTT GCCCTATGGC GGCCCTCACA GACCTCTCAT
 51 TTATGTATCG CTGGTTCAAG AACTGCAATC TGGTTGGCAG CCTCTCAGAG
101 AAGTACGTCT TCATCACAGG CTGTGACTCT GGCTTCGGGA ACCTGCTGGC
151 CAAACAGCTG GTTGATCGGG GCATGCAGGT GCTGGCTGCT TGCTTCACTG
201 AGGAGGGATC CCAGAAACTT CAGCGGGATA CCTCCTATCG GCTGCAGACC
251 ACCCTACTGG ATGTCACCAA GAGCGAAAGC ATCAAGGCGG CGGCCCAGTG
301 GGTGAGGGAC AAAGTGGGCG AACAAGGCCT CTGGGCCCTG GTGAACAATG
351 CTGGTGTGGG CCTGCCCAGT GGTCCCAACG AATGGCTGAC CAAGGATGAC
401 TTTGTGAAGG TGATTAATGT GAACCTGGTG GGACTGATCG AAGTGACCCT
451 TCACATGCTG CCCATGGTCA AGAGAGCCCG GGGCAGGGTT GTCAACATGT
501 CCAGCTCTGG TGGTCGTGTG GCTGTCATTG GTGGTGGCTA CTGCGTCTCC
551 AAGTTTGGCG TTGAGGCCTT CTCTGACAGC ATAAGGCGTG AGCTCTACTA
601 CTTTGGGGTG AAAGTCTGCA TCATTGAGCC AGGGAACTAT CGGACAGCCA
651 TTCTCGGCAA GGAGAACCTG GAGTCACGCA TGCGAAAGCT TTGGGAGAGG
701 CTGCCTCAGG AGACCCGGGA CAGCTACGGA GAGGATTATT TCCGCGTCTA
751 TACTGACAAG TTAAAAAACA TAATGCAGGT GGCAGAGCCC AGAGTCAGAG
801 ATGTCATCAA CAGCATGGAG CATGCTATTG TTTCCCGGAG CCCTCGCATC
851 CGCTACAACC CTGGCCTGGA TGCCAAACTC CTCTACATCC CTCTGGCTAA
901 GTTGCCCACC CCTGTGACAG ATTTCATCCT AAGCCGGTAC CTTCCAAGGC
951 CAGCGGACAG TGTCTAAACT GGGGAGGATC AATGGGTCAG TGG  (SEQ ID NO:1)
```

FEATURES:
5'UTR:        1-25
Start Codon:  26
Stop Codon:   965
3'UTR:        968

FIGURE 1A

Homologous proteins:
Top 10 BLAST Hits

```
                                                                            Score    E
CRA|18000004994221  /altid=gi|1710629   /def=sp|P50169|ROH1_RAT RE...        351    8e-96
CRA|18000004988853  /altid=gi|841197    /def=gb|AAB07997.1| (U18762...       350    2e-95
CRA|18000005023154  /altid=gi|1710631   /def=sp|P55006|ROH3_RAT RE...        348    7e-95
CRA|335001098691669 /altid=gi|11440542  /def=ref|XP_006765.1| mi...          342    3e-93
CRA|18000005126810  /altid=gi|6677697   /def=ref|NP_033066.1| reti...        341    7e-93
CRA|18000005161570  /altid=gi|4506571   /def=ref|NP_003699.1| micr...        341    7e-93
CRA|18000005178954  /altid=gi|3859946   /def=gb|AAC72923.1| (AF086...        337    1e-91
CRA|18000005156283  /altid=gi|8567342   /def=ref|NP_059501.1| reti...        334    1e-90
CRA|18000005097711  /altid=gi|2338748   /def=gb|AAB67236.1| (AF016...        332    4e-90
CRA|18000005010835  /altid=gi|1710630   /def=sp|P50170|ROH2_RAT RE...        331    1e-89
```

EXPRESSION INFORMATION FOR MODULATORY USE:
library source of cDNA clone:
Human Placenta

FIGURE 1B

```
  1 MAALTDLSFM YRWFKNCNLV GSLSEKYVFI TGCDSGFGNL LAKQLVDRGM
 51 QVLAACFTEE GSQKLQRDTS YRLQTTLLDV TKSESIKAAA QWVRDKVGEQ
101 GLWALVNNAG VGLPSGPNEW LTKDDFVKVI NVNLVGLIEV TLHMLPMVKR
151 ARGRVVNMSS SGGRVAVIGG GYCVSKFGVE AFSDSIRREL YYFGVKVCII
201 EPGNYRTAIL GKENLESRMR KLWERLPQET RDSYGEDYFR VYTDKLKNIM
251 QVAEPRVRDV INSMEHAIVS RSPRIRYNPG LDAKLLYIPL AKLPTPVTDF
301 ILSRYLPRPA DSV  (SEQ ID NO:2)
```

FEATURES:
Functional domains and key regions:
[1] PDOC00001 PS00001 ASN_GLYCOSYLATION
N-glycosylation site 157-160 NMSS

[2] PDOC00005 PS00005 PKC_PHOSPHO_SITE
Protein kinase C phosphorylation site

Number of matches: 7
1    24-26 SEK
2    62-64 SQK
3    70-72 SYR
4    85-87 SIK
5   185-187 SIR
6   243-245 TDK
7   272-274 SPR

[3] PDOC00006 PS00006 CK2_PHOSPHO_SITE
Casein kinase II phosphorylation site

Number of matches: 6
1    22-25 SLSE
2    31-34 TGCD
3    76-79 TLLD
4    81-84 TKSE
5   122-125 TKDD
6   233-236 SYGE

[4] PDOC00007 PS00007 TYR_PHOSPHO_SITE
Tyrosine kinase phosphorylation site 64-71 KLQRDTSY

[5] PDOC00008 PS00008 MYRISTYL
N-myristoylation site

Number of matches: 6
1    32-37 GCDSGF
2    38-43 GNLLAK
3   162-167 GGRVAV
4   169-174 GGGYCV
5   194-199 GVKVCI
6   203-208 GNYRTA

[6] PDOC00060 PS00061 ADH_SHORT
Short-chain dehydrogenases/reductases family signature 159-187 SSSGGRVAVIGGGYCVSKFGVEAFSDSIR

Membrane spanning structure and domains:

| Helix | Begin | End | Score | Certainty |
|-------|-------|-----|-------|-----------|
| 1     | 129   | 149 | 0.700 | Putative  |

FIGURE 2A

BLAST Alignment to Top Hit:
>CRA|335001098691669 /altid=gi|11440542 /def=ref|XP_006765.1|
        microsomal NAD+-dependent retinol dehydrogenase 4 [Homo
        sapiens] /org=Homo sapiens /taxon=9606 /dataset=nraa
        /length=317
        Length = 317

Score =  342 bits (869), Expect = 3e-93
Identities = 162/313 (51%), Positives = 228/313 (72%)
Frame = +2

Query:  26  MAALTDLSFMYRWFKNCNLVGSLSEKYVFITGCDSGFGNLLAKQLVDRGMQVLAACFTEE  205
            +A    L ++  W++    ++   L +KYVFITGCDSGFG LLA+QL  RG++VLAAC TE+
Sbjct:   5  LAVFVGLYYLLHWYRERQVLSHLRDKYVFITGCDSGFGKLLARQLDARGLRVLAACLTEK  64

Query: 206  GSQKLQRDTSYRLQTTLLDVTKSESIKAAAQWVRDKVGEQGLWALVNNAGVGLPSGPNEW  385
            G+++L+  TS RL+T  LDVTK+ES+ AAAQWV++  V  ++GLW LVNNAG+ LP+ PNE
Sbjct:  65  GAEQLRGQTSDRLETVTLDVTKTESVAAAAQWVKECVRDKGLWGLVNNAGISLPTAPNEL  124

Query: 386  LTKDDFVKVINVNLVGLIEVTLHMLPMVKRARGRVVNMSSSGGRVAVIGGGYCVSKFGVE  565
            LTK DFV +++VNL+G+I+VTL  +LP+V+RARGRVVN+SS  GRV++  GGGYC+SK+GVE
Sbjct: 125  LTKQDFVTILDVNLLGVIDVTLSLLPLVRRARGRVVNVSSVMGRVSLFGGGYCISKYGVE  184

Query: 566  AFSDSIRRELYYFGVKVCIIEPGNYRTAILGKENLESRMRKLWERLPQETRDSYGEDYFR  745
            AFSDS+RREL YFGVKV +IEPG ++TA+  KE         ++W+R   E +++YGE +
Sbjct: 185  AFSDSLRRELSYFGVKVAMIEPGYFKTAVTSKERFLKSFLEIWDRSSPEVKEAYGEKFVA  244

Query: 746  VYTDKLKNIMQVAEPRVRDVINSMEHAIVSRSPRIRYNPGLDAKLLYIPLAKLPTPVTDF  925
                 Y   +  + Q     +  V N MEHA+++   PR RY+ G DAKLLY+P++  +PT + D
Sbjct: 245  DYKKSAEQMEQKCTQDLSLVTNCMEHALIACHPRTRYSAGWDAKLLYLPMSYMPTFLVDA  304

Query: 926  ILSRYLPRPADSV  964
            I+    P PA ++
Sbjct: 305  IMYWVSPSPAKAL  317  (SEQ ID NO:4)

Hmmer search results (Pfam):
| Model | Description | Score | E-value | N |
|---|---|---|---|---|
| PF00106 | short chain dehydrogenase | 160.4 | 1.2e-44 | 1 |
| CE00062 | CE00062 steroid_dehydrogenase | -111.2 | 3.1e-06 | 1 |

Parsed for domains:
| Model | Domain | seq-f | seq-t | hmm-f | hmm-t | | score | E-value |
|---|---|---|---|---|---|---|---|---|
| PF00106 | 1/1 | 26 | 208 .. | 1 | 203 | [] | 160.4 | 1.2e-44 |
| CE00062 | 1/1 | 23 | 309 .. | 1 | 337 | [] | -111.2 | 3.1e-06 |

FIGURE 2B

```
   1 CCTCAGCAGT CTATGCTCTC CCACTGGAGG GAAATGGCCT GGCAGAGGAG
  51 AGGGCTCCTC TCCTCTGAGA TACCTGTGTG CATGGGGTGG GGATGGGGAG
 101 TGCAGCTACC AACCTGACCT ATCAGACCTT AGGGGCCAGC TTGGCAAGGA
 151 ATGCTGTCAT CTGAGAGAGG GAGGCATTTC TAGCCCTGGG AAGAAGAGCC
 201 TTCTATGTGG TCCTACCTCC CTCACACCCC CCACCCTCAT GGACTGTGTG
 251 TTTAGTTTGA GGCCAGGGGA ACACTGCCAG CATAGAGGCC CAGGAGGTGC
 301 TGAGTCAGGC CCAGGCCTGT GCTGGGGCAG TTCTGAGTTA TCCTTATGCT
 351 AAGTCAGACC CAACTCCTGG ACCTCACCTG TGTCCTCAAG GACTGGGATA
 401 CCCAATGCCC CGGACCTGCT CAGTCTTGAG TGACATGGTC TGACCTGTTT
 451 CAGCCAAGAC TTCTCTGTTC ATTCACCCAG GAGGCAGACA GAGACTGGGA
 501 GATTGTTCCC AGATCCCGCA TAGGAGGTGC TCTGCCTCGG GTTGGTTATG
 551 AAGTAGGTGT GGTTTGCTTT CTACCATTTC CCACCTCCAT CCCCTATAAG
 601 CTTTAGGTCT GCTCTTTGGG GGTGGGTTCA TAATCTGGCC CCCTCCCCTA
 651 CTTTGTTAAG GAACGGCCAA ACCCTGCGGG GCTTTCCCAG GGTGACACCT
 701 GCTTTATGTG ATTCCACGCT GGTCAGACTT GGCAAATGGT GGATCACAGA
 751 GATACATCCT TTGTCCCTTC ACACTAGAGA ACTTTGTGGT CCCATTTCTG
 801 TGTCAGACTC GCTAAGCCAT GAAGGTGTGA GCTAGGACCA GGCTCATCCC
 851 AAGGAATGGT GACCCTAGAT GTTGATCCAA AGAACCACAG AGGCTCCAGC
 901 ATCATTCCCT GCATCTTATG CAATTCTGGG TGTGGCCCCT CACTACTCAC
 951 ACCTCTGGTT TCCTTATTTC CTTTCCTTTA CCACCTTACC TCTTAGCTTT
1001 CTGTAAATTA TTTGCTAAAT TGCCTAGAAT CTCTGTTTCT CCTCCAAGTC
1051 CCGACCCTGA GAATTTTCTA TGTCTCTGGC CCCAGTTCTC TGCTCCTCCT
1101 ATATCTCATC CCCTCTTACA GTCAAGGCCT CTGCCCAGAC AATTCCCTCA
1151 GCTGCCCAGT GAACTCATGA TCCCTCCTCA TCATCTTGCC CAGGGCTGCT
1201 TACTGGTGAC CTGAGTATGA CCCCCACAGG GTGTCAGGCC TGAGTCCCCC
1251 AGGTCTTTCT GCTTTCTGGT GGCTAAGCTT CACATGCCAG CCTCCCCTAT
1301 AGGAGGGCCC TGCTGCCTCT AGCCTCAGGA CAATGGAGGT ACATCCACCC
1351 TAGGAGAAAT CCATTGCTTT TCATCCTCTC TCATGATGGA GACTTACCTA
1401 AGAATTCCAG AGAGCTGATG ACCTGCGACT TGTTTCTCTT GGGGTTTGGA
1451 AGGTACAGAA CCAATGTTGT TTGTTTTACA TTAATAAATT TGTCTTGAGT
1501 ATTTTCCCTG AAAATAAACT TATTTACATA CCTGCACTCA CGACAAATGA
1551 TTTTGATCCC TGGAGACCAA AATCCCCAGG CTGGGTTGGG GGCAGGGTGG
1601 GGACAGGATT TCTAGGGGAG CTGTCTGGGG TGAGTCCTCA TCTTTCATTT
1651 GCCTGCCTTA CACCGCCTGG GTGAGCCACC ACTCATCACC AACATTACAA
1701 GTGGATTATT TCCAATTCTT GGCAGCTTTA CCCATCAGGG CAGGGGGAGA
1751 GAGGGAGGCA GCTACCAGGG CTGTCAGAGG TGACAAGGCT TCAGGTTGGA
1801 CTTGAATTTC TTGCATCTGG GCTAATTGCT GTGGTGATGC ATCCACCTAT
1851 AAAAATTACA GCGTGGCTCA CCCAGGGACC TAGATTTGTT GCAAGCTGTG
1901 GGAGGAAGGA GAGTTCTTCT TCCAGGTGGT TTCCTGCAGA CTGCCTGCTA
1951 GGGCTCAGAG GACCAGCTTC TTCCCTGCTG TCTCCTGAGC CCAGTCCCTC
2001 TTGGCCATCA CATTCCCCTT GCCCTATGGC GGCCCTCACA GACCTCTCAT
2051 TTATGTATCG CTGGTTCAAG AACTGCAATC TGGTTGGCAA CCTCTCAGAG
2101 AAGTACGTCT TCATCACAGG CTGTGACTCT GGCTTCGGGA ACCTGCTGGC
2151 CAAACAGCTG GTTGATCGGG GCATGCAGGT GCTGGCTGCT TGCTTCACTG
2201 AGGAGGGATC CCAGAAACTT CAGCGGGATA CCTCCTATCG GCTGCAGACC
2251 ACCCTACTGG ATGTCACCAA GAGCGAAAGC ATCAAGGCGG CGGCCCAGTG
2301 GGTGAGGGAC AAAGTGGGCG AACAAGGTGG GGCGAATTAC ATTCTTTGGC
2351 TTTCTTGGTT TCTCCTTCTT CCTCTTCCTC TCTCCCGAAG CATCTGACAG
2401 TATCAGAGAC CCTGATGTCC AGATTGGGTG GGAGGGGTGA TGTAGGGAAA
2451 GGCCCCTGCC TCAATCTGAT TGGAAGCCAC TGCATGGTTT GGCCTGTTCA
2501 CATGAAGGGG TGATTTCCCA AGGAAGTTTT CTGTCCTGGA AACTCAGAGA
2551 AACGGGAAAG AGGTCTCAAT AGGAAGCGAG GGGGGAAGAT GTGTTCTGTG
2601 TGTCCAAACC TCTAAAAATG GACGTGCCTG GCTGGGCGTG GTGGCTCACG
2651 CCTATGAGCC CAGCACTTTG GAAGGCCGAA GTGGGAGGAT CATGAGGTCA
2701 AGAGATCGAG ACCATCCCGG CCAACATGGT GAAACCCCAT CTCTACTAAA
2751 AAGTATAAAA ATTACCTGGG TGTGGTGGCA CGTGCCTGTA GTCCCAGCTA
2801 CTCAGGAGGC TGAGGCAGGA GAATCACTTG AACCCGGGAG GCGGAGGTTG
2851 CAGTGAGCCA AGATTGCGCC ACTGCACTCC AGCCTCGTGA CAGAGCAAGA
2901 ATCCCTCTCA AAAAGAAAAA AAAGAAAAAA AAAGGATGTG CCTCTCTGAT
2951 GTTTCAGCAG TCCTAACCAT CAGCTCCTGG GGAAATACAA ACACATTTCT
3001 TGTTGGGATC AGGATGGGGG AGGGGAATG AGACAGGAGG CTGGATCCCA
3051 TGAGTGGGTG CAGTTTGTCT CCTTGACTAT GTCAGGCAGG GGAGAAAGCA
3101 ATCTGGTCTC TTCTTGACAT CATGGTGGGT GTTGATTTGA CTTCAGGGCA
3151 AGTATGTATG TCACAGTGGC TGCTCCTATT GGGAAGGAA GCTGTGGACT
3201 GGGGCTGGCC CAGGACTGTG TGGGGACCTG CCTCATGCAC TTCCAGCACA
3251 CAGGGTGTGG GCCCAGGAAC AGGAGGAACA GGATGGCTGA GTTGCAGAGA
3301 CAGCAGACTA GAGGAAGTCC TCCCTCCTAA AGGAACTAGT CTGGAGCCCA
3351 TGCGCAGGTC AGGGCAACAG AGCCCTGGAG CCAGGGGAT CTAGACAGTA
3401 ACTCCCTGCT TGATTCTTCT CCTTAGCACT TATCACTAGT CAATGTACAA
3451 TAGATTTTAC TTATTTATTG TCTGTTTCCT CTGCTAGAAT AAAGCTTCCT
3501 GGGGACAAGG ATTTTTGTCC CTTTTATTTA CTGTACATCC TTAGTACCTA
```

FIGURE 3A

```
3551 GAATAATGTC TGGCACCTAG TAAGGTACTG AATAAATAGA TTTGAGTGAG
3601 CTAATTAATT AATAATTCAG CAAGAGTGAG CCTCTGTCTT CAGCAGGCTG
3651 TCTCAGCCAG TTCCCTACAT TCAGCCTTGA GCCACTTGCC TTAATACCTC
3701 ACTTAGCATG TGAGTTTCCT GTTGCTATTG TAACAAATAA CACAACTGTG
3751 GGGGTCTGAA GACAATACAA ACATATTATC TTGTAGTTGT GGAGGAGTAA
3801 TGTCTAAAAT AGGCCTCACT GATCTAAAAT CAAAGTCAGC AGAGCTGTGT
3851 TCCTTCTAGA GGCTGTAGAG GAGAATCCGT CTCATCGACT TTTCCAGCTT
3901 CCAGAGGCAG CTGGCATCCC CTGGCTCCTG GCCTGCTACC TCCATCTTCA
3951 AGGCCCGCAA GGTTGGGCCC AGTCTTTTTC ACACTTTTCT CAAGCTCTCT
4001 GATTCTCCGG TTTCTGCCTC TTTCCACTTA GGACTTGTGA TTATATTGGG
4051 CTCACCAGGT TAATCCAGGA TAATTTCCCT GTGTTAGCTT CCTCCCTAAC
4101 TTTAAGGACA ATTAATTAGC AACCTCCATT CCACCTGCAA CCTTAATTCC
4151 CCTTTCCCAT GTAATCCAGC AGATTCACAG GTTCCAGAGA TAATGAGGAT
4201 GGGGACATCT TTGGGGGACC ATTATTTTGC CTAAGCCACT TGGCAATATC
4251 CTGGTCTAAG AAACACTGGG AACTGGGGTG GGTAGGGGGA TGGGAGAGGA
4301 AGTTCTTTCA TGCTTTCTCA TTGCTCCTGA ATGGAGAAAG GCAGGGAGAC
4351 TGGGTAGGGG CATGGCTTGG GTGGGGACCC CAGCCCTAGA GGGAGGGGTG
4401 GACTAGGATT TATGTTTGTG TTGAGACCTG CCCTCAGGAG ACAGTGGGAT
4451 GCGCCTGCAG AGTATCTTGG GGCTGCTGAG GCTGGGGCTG TGGTGCGAAT
4501 CACCAGGCAG TAGGACTTGG GGAATCCTTG CATGAAGGAG CTGGAAGGGG
4551 TCCTTGAGGA GTGTTTAGAG GGGTTTACAG TAGAACCCCA ATATGTAAAA
4601 CAAATGAAAG GAGAGCTTCT CCTGCATTTT CCTCCCCCTA GAAGGCTTGC
4651 AAAATACAGC CTGGAAACAA CTGTTTTAGT CTAATCTGAT GAAGAGCCTG
4701 AGGCCCAGAG AGGGAAGTGA CTTGTTCAAG GCTGGAGGTA AAACCAGGAC
4751 TGGACCTGAA GCTCTTCAAC CCTGGGCCCC TGCAGAGTTG AATGACAACA
4801 CTTAGCATTA TTTCTTTCCA TTTGTACCAA CCTAATTGAA ATATCTCAAG
4851 GATAGTCCTC ATCACATTTT CCATAATTAT TTTATTTAAA TATTTTATAT
4901 ATTTATTTAT AAATATTATT ATTTCCTTCT AGGCTTGTGA GTTCCTTGAG
4951 GGATAAGATG CTGTGTTGTT CATTTTATGT CTCCTTTGCC CTGTATTTTA
5001 CTTTATTTTA TTTTATATCG TTTTATTTCA TTTTATTTTT AGAGACAGAG
5051 TCTCACTCTG TCACCCAGGC TGGAGTGCAA TGGCACCATT ATAGCTCACT
5101 GTAACCTCGA ACAAGGTAAC CTGTAACCCG GGCTCAAGTG ATTCTCCCAC
5151 CTCAGCCTCC CAAGTAGCTA GAACTACAGG CACATACCAC CACGCCTGAC
5201 TAATTTTTTT TCTTTTTTTG TAGAGACAGG GGTCTTACTC TGTTGCTCAG
5251 GCTGGTCTCA AACTCCTGGC CTCAAGTGAT CCTCCCACCT CAGCCTCTCA
5301 AAGGGTTGTG ATTACAAGTG TGAGTCACTG CACCTGGCCT CCTTCACCCT
5351 GTAATTGTCA CAGACTAGAT AAATGCATGA ATAAATGTGT GAAGATGAAT
5401 GAATGAATGG ATTGATTTTG GTAGTATGTG AAATGCAGTT GGTTATACTT
5451 AAGTGAATAG AGAGGGAGAA GTATGATGGG GAAGGGATCT AAACATTAAT
5501 TCATTGGTAT GAAAATGAAA CTCTTATCCC AAAGCTGATA GCTGAAATGC
5551 TGTCACCTAA CACCTCGATT GTAGCTAGTA CAGAGCGCCA GCTAGCCGGC
5601 AGACTTTATG TGAATCAGGA AAAAGTGTCC CTTCAGGGAA AACGAGTTAG
5651 TAAAAGACAC ACCTTCCTTT TATGTTATAG CCTGACCGAG TTATGTCTTG
5701 TGCACCTGCT CAACCATCCT TGAGGGCACT GAGCCGGTGG GGAGCAGAAC
5751 TTGGTTCTTT CCCAGGCCCA CTGATGATTT CTGTGTGGTT CATCTCACCC
5801 CCAGGCCTCT GGGCCCTGGT GAACAATGCT GGTGTGGGCC TGCCCAGTGG
5851 TCCCAACGAA TGGCTGACCA AGGATGACTT TGTGAAGGTG ATTAATGTGA
5901 ACCTGGTGGG ACTGATCGAA GTGACCCTTC ACATGCTGCC CATGGTCAAG
5951 AGAGCCCGGG GCAGGGTTGT CAACATGTCC AGCTCTGGTG GTCGTGTGGC
6001 TGTCATTGGT GGTGGCTACT GCGTCTCCAA GTTTGGCGTT GAGGCCTTCT
6051 CTGACAGCAT AAGGTAACTG GGCCCTGGTA CTGAACAATT CTGGGTGAAA
6101 ATCCCAGAGA TTAGAGAGGG TTGGGAGTGA CAGCATGTGG GCAGGGGAAT
6151 TCCGCAGACA GGAAGCTAAC ACAATAGCAG AAGGAAGGTT AGACCTCAAG
6201 GTGCTTTCTC CAAGGACCAA GAGCAGGGAT GAGGAGAAGA GGTAGGGTGG
6251 AAATACAAGG CATCAGGTGG GCCTTCCCTT GAGCGGCACC AGGGTGAGTG
6301 AAACCCTGTT TGGGCCTGTG AGAGGAGGGA GAGTCCCCCA AACAGACAGA
6351 CAGGCCTGGA GGCACAGGTC CCCTCTGGGA GGTCCTTAGA GGAGCGTGCA
6401 GGCCTTGTGT ATATCCACAC CATTCACCGT GTGGGTGTTG AGTGAGGGGT
6451 TGCTAATGGG AGGGACCTGG TGGGAGGCAA GGCTTTGGCC TAGATTCTCT
6501 ATTGACTTCT TCCCGCTGGT TGTGCCTAAT GCAAATTGCC CAGAGACTGC
6551 TGGGCCAGTT TTGGAAAGGG CTGAGTCCCT AAGGAAGGGC TTATTTGCAC
6601 AAAGGCAATG CCAGGGCCAA GTACAGGGGT GAGAGAAGCA TCTCTAGGTT
6651 CCTGAAAGAC CAGCCCATCC AGAGGTGACT CTCCGTGATG ATTGTCATCT
6701 TGGGCCCAG ACTGACTGCA ACTCTTCTTT CCCAGGCGTG AGCTCTACTA
6751 CTTTGGGGTG AAAGTCTGCA TCATTGAGCC AGGGAACTAT CGGACAGCCA
6801 TTCTCGGCAA GGAGAACCTG GAGTCACGCA TGCGAAAGCT TTGGGAGAGG
6851 CTGCCTCAGG AGACCCGGGA CAGCTACGGA GAGGATTATT TCCGCATCTG
6901 TAAGTTCCTG GGGCAGGAGA GGGGTCTCTG AGGGGGGCGA GTGGGTCTTG
6951 GGGTCATTAG CTGGCTTTCC GTTTACAGAT GGTGAGACAA AATGCAGAGG
7001 AGTTCAGGAC CCAAGGTCAC ATAGTGGCAC AGCTGGGGTT TGAGAATAGA
7051 GAGCAAGTGG CAGAATCATC ACTTCTGGAG CAGCCCGGGG AGTTAAGGGC
```

FIGURE 3B

```
 7101 AATTCAGCCC ACTCCTGGCA CCTGCCCCCA CAGCATCATG ATGCAGGGGA
 7151 ATCAGGTGAA AATGCACTGA GATAAATACA GCAAAGAGAT CAAGGGCATG
 7201 GCTGCTGGAG CCGGACTGCC TGGGTTCAAA TCCTGGCTCT ACTACTTACC
 7251 AGCTAGGAGA CTTTGGACCT ATTACCTAGT TTTCCCATGC CTCAGTTTTC
 7301 TTATTTACAA AATGGAGCTA AAGATAGTGC CTCCCTCATG GGGTTGTTAT
 7351 GAGGGTTAGT ATGTGTGAAG TACTTTGCAC ATTCTGAGTG CTTGTTAATA
 7401 AAGAAGAAAA TGAGCACATG GGGATTTAAA AGGGAGGGTC TCTAGGCAAC
 7451 TCTCTTTCTT TCCCTGAGCT GAGGGTCTCC TGTGAATCAT AGGTGTTTTT
 7501 GGAGGGTAGA GGTGGGACAC GGCAGCTGTT TACCCTGCTG CCCCAAAACT
 7551 TTCTGCCACG AAAGTTGTCT GCTGGATGTC GTACGTCAAC AGAGCACAAA
 7601 GCCAAGTCAG CCATTTTTTT CACTTAATAC ATACACACTT TATTGCATTT
 7651 TTGTTTTTTG TTTTTGTTTT GAATCAGTAA TACAAAGCAT GCAAGGCTGC
 7701 CATGTCCCAA GCCTGTGTGG GGCTGGAGAG CTGGAGCGGA CACAGCAGTA
 7751 TGCCTGCCCT TCACTGCCTG TAGCTTATGG CCCAGTAGGG GAGACAAACA
 7801 TAAATCAAAA CACATGTGTT TATGGTAGAT GTGGATAAGT GCTACAGAGG
 7851 AGAAACAGGG TTGTGAAAGA AGAATGGAGC AGGAAGTTGC GGTCCCAATT
 7901 CAGACTATGG TGAAGGGGAG AGCTTCTGAG TTGACTTTGA GGAGGAATAA
 7951 GAGTTAGGTG TTGCTGGGAA GGGGAAAGAG GGGATGCGTA GGGACTTTTT
 8001 TTCTGCAGGA AGGCTCTGAG GCAGAAAACT CCATTTGAGG AACTTTAAAG
 8051 AAACCAGCAG GTGGGAAGCA ATGGGAGGTA GCTGGGGTAT ACGGAATAAA
 8101 TTAGAGCATC AAAGCACACT GAGGATTAAG GGGTGAGGGA GAGGAAGCTA
 8151 TCAAGGGTGA GTGTTAGCTT TACAGCTTGA AGAACATGGT GAATGGAGGT
 8201 GTCTTCATTC ATTGATTTAG GGAAGTCTCA GGGAAAAATG TTTGGAGTAC
 8251 TCCTTAGATA AATTCATCTT TTAGTGCTAA ACATGTTAGG ATTCTGTGAG
 8301 AAGAAAATGT CTAAGGATTT ACACTAGTTG GGACTTACTC AGTGACAGAA
 8351 GATCCAATGC AAATTATTTA AGCAGAAAAG GAATTTCTTG CCTCACCTGA
 8401 CTAAAAAGTT GAGCAAGATA AGCTTCAGGT ACAACCTGAC CCAGACTGCA
 8451 AATGATGTTG CTAGGACCTG GTTCCACCCA TTTCTTGGCT CTGCTTCTTT
 8501 TGCACTGACT CCAGTCTCTA AGCTCTCTCC CCTGTGGGAG CCACATTGCT
 8551 GCAGCCTCTC TTCACCTCCA CCTAGGGTGA GGTCTGCTGG GAAAATAGGA
 8601 GAGTTATTTC CAGTACCTCT CCCAAAAGTC CTAATGTACA CTCCGACTTG
 8651 GAGGACCTTA TGGTGACCGC GTCATGGGGG ACCACAAGAT GCACCCAACC
 8701 CTAAACCAAT CACTGCTCAG AGGGGAATGT GAAGGTGTGA TTGGCTCAGG
 8751 CTGGGCTGTG TGCTCTGCCC AGACCAATGG ACACAGTGTG GGGGAGGCAT
 8801 AGGTCCCCAG AGGGAAATCT GCAGCTGTTG GGAACAAGGA GAGAAGATGT
 8851 TAGCATGTGT GGGGAAGAAT ATTTATCCTC TGTGTGATCA TTCTTAGCAA
 8901 AGAGTAGTTC AAATTATTTG TGGAGCTGCT TGGAGGCTGG GGTGAAATGG
 8951 GTTCAGCCAG TGTCTGGAAA CCTCACAAAG TCATTTTCTA AGTAAGCACT
 9001 CAGGGTGAAG AGAGCTTGTA GCATCTTTAG TGTGGTCCAT GAAAGAATAT
 9051 GTATAAAGGC AAACTCCTCC GAAAACCTTG TCCAAAAGCT AGTATTGTAC
 9101 TAAAGAATAG TAAGGATTGG GTTTATAAAA TATCTTAGGC CAATTCACCT
 9151 GTAGTCCACA CCATAATTTC AGAGGAAAAT TTTCAGGCAG TGGTCAACTA
 9201 CATTTAGATA AACGTTTTCC CAAGTGGTTA TACTAGAATT TTTGCTTCAG
 9251 TTGCCCAGTG TTTATTGGGA TTCAGAGATG AGACACTCTC CAGGAAACTA
 9301 GCAGGGAAGA TGTGAAAGCA AATACACCAC CACATGAAGA ATCTTGCTAT
 9351 AATGGACATG CATACAAAAC AAAGCAGCAA TGCAGACTTC ATTCTGCTGT
 9401 CACAGAAGCC TTACAGAGGT GACAGTTAAT GCCTTAGTGA GTTTTGAAGG
 9451 ATGAATAGGA GTACACCAAA AGGGAAAGAG ATGGCGGATG TTTCACACAA
 9501 GAGGAAGGGT GTGAGCAACG TTTTAGTGAC CTGACATAGC ATTGTATGCT
 9551 TTTGGAGGCA GTGCAGATTC AGGCTTGTAT TCCAGCAGTC CCTCTAATCA
 9601 TGTTGTATAG CTCTCCAAAC TTGTTTATCC ATTTATAAAG TACAATTCCT
 9651 CTCTCATGGA TTGTTAGGAG AATTAAACAG AAATGCAAAG TTCTCAGCTC
 9701 TGCTACAGTA AGAGCTGAAC AAACCTTTGC CATTGCCATT ATAGTCTGGC
 9751 AGGAGTGCTG TGGGTGATGA TTGAGGAGGG GAGAGATTAG GAGTCAGATC
 9801 ATGAAATGCT TTGATTGCTA TAGTAGGGAG CATGGCTCTT ATCCTAAAGG
 9851 CATTAGAGAG CCTTGTAAAT GGCTCTGAAA TGAAGGATCA GATTTGTGTC
 9901 ACCGTGGGAA GGAATAAAAA GTCCACCTGG GGGACTACTG GCAGAAACCC
 9951 AGTGAAGGAA CGATAAAGAC ATGAAGTTGT AAGTCCCTGA TGGTTCTGGT
10001 GGTGGGGGT GGCTATGTGA CAGACAGAAG AGATATTTAG GAGTAGTCCT
10051 AGAGCATCGC TGGGTACAAA CTCAGCCAGT TGCTGTGACT GACCAAACAG
10101 GCCCCTGGCT TGTAACCCTC AGGACCAGGC CTGATACTTT ATAGATTTTG
10151 TCCTGCTTAA TTCTCCCAAT AACAAAAACA TTTTCCCAGG TGCCCAGCTC
10201 CAAAGCCTAT GTCCTTCCTC ACTGTGAAGG AGAGTGACAA AGCTGGATGG
10251 GTCCTTCCGT CTCCCATCCT ACTCCATGCC TAGCAGGGTG CCCAGCACTG
10301 AATGGCAGCT AATATCTATT TGAGAAAACA ATGAAAGCAA GTGCCTCATA
10351 CCATTCCCCA TGTCTGGGGT AACTTCTCCC ACCCCACTGC CTGTGCAAGG
10401 CCTCCCCACC TCTCAGAACC CAGTCCCCAG CCCATCTCAC CATGTCAGCT
10451 TGCTCCACAT CCTCAGCCCA CAAAGCTTTC CCTGGCGCCG AGGGGGCAGA
10501 GAGAGCCTCC TGGGCATCCT GAACGATTCC TTCGACCCTC AGCCCTGCTG
10551 CTGGTGGCCT CTGTGCCAGC TCTACGGTCA GAGGTCAGGG TGTGGCTTCC
10601 TAAGACATTA CTGCTTTATG GACAGTCTGG CTTTGAGTTA GTGTGGCTCT
```

FIGURE 3C

```
10651 TGTTGAGATC CCAAAATATA GTTTGGCTTT TCCCCTGCAT CAGTTTTCTT
10701 TCCAGGAAAC AGAAAATGGA GTTTCTCGGA GTCTGGGGTT AAGGGGACTG
10751 AAGTGATGCT GCCCCATTCT CACCAACCAC CCACAAGGGT CCTGGCCCCA
10801 AGCGGGTGAA TTCCTTGCCT GCCTGGACCA TTCTCAAAGT CAGGGCAGCT
10851 TTGGCTTCCT CTCCATTTTC AAGTTTTCAT ACCTTATCAG GGCAGTCTGA
10901 CTTTGAAGCA TCATTTTCCC TGGAGTCCTC AGGGCTCTCA ATGAAGCATG
10951 AATCCCCCTG TCCTGGGGTG AGGATGCAGA TGAGGGCCTG GTGGGTGTGT
11001 GGTGTGGCCC TTCTCCCATT TATGTCATGA ACTTTGGCAG ACTTGTACTA
11051 TTTGGGTGCT CTGTCCCCAT CTCCACCCCT GTGGGTCAAT GCAAACAGAA
11101 CAACTCCTCA CATTTGTGAG GGCCCCACGA GGTGCTTGTC TATGCCTTAG
11151 ATTATTTGAG TGACAGTGGC CTTATGACTG AGGTAGGGGC AGTATTACTA
11201 TTTTTAAATA ATATTTTCTC CTGCATGTTT TTGTTTAAAT GTGGGAACTC
11251 TAGGAAGTAC ATAGAAGAAA AAAAAAGGG CTGTTTTCCC ATCATGTTTG
11301 CTCTTCTGTA CTCCCCCAGT GTCTACCCTG CTGTTAATCA TCTTTGTTAT
11351 TCTCCAGGAC AGATATTTTT TGAGATGGAG TCTCACTCTG TTGCCCAGGC
11401 TGGAATGCAG TGGCGCGATC TTGGGTCACT GCAACCTCCC ACTCCTGAGT
11451 TCAAGTGATT GTCATGCCTC AGCCTCCTGA GTAGCTGCGA TTATAGGCAC
11501 GCGCCACCAC GCTCACCTAA TTTTTGTATT TTTAGTAGAG ACAAGGTGTC
11551 ACCATGTTGG CCAGGCTGGT CTCAAACTCC TGACCTCAGG TGATTGGCCT
11601 GGCTTGGCAT CCCAAAGTAC TGGGATTACA GGCCTGAGCC ACTATGCCCA
11651 AACTTTAGGA AAGATAGTAT TATCTCCATT TTATAGACAA TAAAAGTTTA
11701 AGCTCAAAGT CATATAACTA ATAAGCGGCA CAGTTATAAG GAGAATGTGC
11751 ACAGTTCTTC TCATCACCAG TCTAATGCAA TAGTAGGACT TCAATGCACA
11801 ATTGTTGAAT TCAGAAAGAT AAATAAGACT ATTTGTTTAT TTATTTATTT
11851 ATTTATTTAT TTTGAGACAC CGTGTCATTC TGTTTCCCAG GCTGGAGTGC
11901 AGTGGTGTGA CCTCGGCTTA CTGAAACCTC AGCCTCCTGG GTTCAAGTGG
11951 TTCCCATACC TCAGCCTCCC GAGTAGCTGG GATTACAGGC ATGTGCCACC
12001 AAGCCCAGCT GATTTTTATA TTTTTAGTAG AGATGGGGTT TCACCATGTT
12051 GGCCAGGCTA AGATTATTTA TAATAGTCTT ATAAATGTGT GTTTGTATAA
12101 GGGACCACCT GGAGGGTGTG GCGGACCTGC CTGAAATGTT AGATCAGGGA
12151 TCTGATGGAA AGGGAACTTG GACGGAATTC GGAAGAAGCC ATCTTTTATG
12201 AAGAATAACA GAGCCTTTTT CCCCTCTCTG CCCTCAAACA GATACTGACA
12251 AGTTAAAAAA CATAATGCAG GTGGCAGAGC CCAGAGTCAG AGATGTCATC
12301 AACAGCATGG AGCATGCTAT TGTTTCCCGG AGCCCTCGCA TCCGCTACAA
12351 CCCTGGCCTG GATGCCAAAC TCCTCTACAT CCCTCTGGCT AAGTTGCCCA
12401 CCCCTGTGAC AGATTTCATC CTAAGCCGGT ACCTTCCAAG GCCAGCGGAC
12451 AGTGTCTAAA CTGGGGAGGA TCAATGGGTC AGTGGAGCCT AGAAGTGGGG
12501 GAGGAAGGAA GGACCGTGGG GTCACAAAAG GTGGTATCGG TTATCCTGGG
12551 GGCATTGGCT GCAAAGGAAG CTTGGCTCAG CTGACACCCA CTGCTGTCGA
12601 ATTTACCAGT AACTTCTAAC AGAAGGTGAA TGCCTCTTCC CACCCTCTGG
12651 GACCCCACAG AAACCTGAGG TGGTCTTTGC AGGTTCAGCG ATCTGCAGCA
12701 ATAGCTCCAA GGACGTCTGT CACCCAATCA GGATACAGCT TTTTCTGGTC
12751 CTGGAAAAGT CATGGAGAAG AAAACCAGCT CCTGTGGAAT CATGAGCCCC
12801 TTTCAGTTAT CACTGCCACT GAGAAATACT CTTGCCTCCA
12851 GGAGAATCTA ACCACCTTCC TAATGGGTCC CTCAATATGC ATAACTTCAT
12901 TCACATAACC CATTACTGAA GTATGCGGTA GGGCAGATAG GGAGTGCAAG
12951 ATTAAATCAG ACAAAGTTT AAAATATTT CTTTCTTTTT AGATTCTTCT
13001 ATCTATAGGT TATTGGGATC CACATGAAAT AACATTCATT TATTTAATCA
13051 CCATTAATTT TTCAAATATT TATTGAGTGC CTACTACCTA CCGGGCACTT
13101 TGTAGGTGCT GGGGGAATAT AAAGATGATT AAATCATGGT CTTGGTTTTT
13151 TATTGTTTAT TTTGTGTTTT GCTTTGCTTT GTTTTAGCAC AATATCTAGT
13201 AGCTGAGTTA GGACAAACAG CGATAGAAGG AATAGAAATC AGAATACAAA
13251 TTTTTAGAGC TATGAAGGAC CCTGGAGGTC TTCATCCAAT ACTTCACAAG
13301 CTTGGCTGTA CCTTGTATCA CCCAGTCAAT TAAAAAATAC AGACTCCTGT
13351 GCCAATATTA GAAAATCTGA TTCAGTAGGA CTGAGATAAG GTCCAGAAAT
13401 ATGTGTTTAT AACAAGGACC TATATGATTC TGATGCACCC GAGCAACTTG
13451 GAGCCACCAA TAATTCCATA GAATAAGTAA CTTAACACTC AGAGGGGGAA
13501 GTGACCTACC CAAGCCCCCA GTTTAGTAAC TAAGACAAGG ATAGAAATGA
13551 GGCATTCAGA CTCCCAGACC AGGATTATTT TTCAGTTATA GGAAAATCAA
13601 TTTCTCAAAT TAGTAACACT GTCAAATAAG TCATTGAACT AATTTTTTTT
13651 AAAAAAAGAC TTAAACTCCT GGGTCATATG AAGTTCTGTG GAAGAGACTT
13701 TTTTTTTTAT CTTGATAAAT GGTCATGTAA TAAAGGTCAA ATGTGATTTT
13751 TTTAACTAAA ATATCTTTAA TTTGGGTCTC TTCAACATAA TCAAAATAATA
13801 AAATATAATC CAGGTACATC TGCAAAGACT CCAAATAAGG TAACACTCAC
13851 GGGTTCCAGG GGTTAGCTTA TAGATATATC TTTAGGGAGC TACTGTGCAA
13901 CTCACTACAG TTTGTTGTTT GCAGCACTTC TATTCCTGGC ACCAAATTCT
13951 AAATCAGATA GAATGCATTC AACAAGTAAC AGAAAAACCA ACTCACACTG
14001 GCTTAGACAA TGAAGAGTGA GGGCAGGGCC CAGTGGCTGA ATGATGGCAT
14051 TGAGGCTGTA GGCTCTTTCT ACTTCTTTGC TCCGCTGCCC ACAGTTTTAT
14101 CTTTACCCTT TGTTGCTGTG GTGTGACTGC CAGGCAAAGG GAACTCTACA
14151 TTTCCTCATT CACAACTTAG AGAAGAAGAA AGAGCCTGCC TTTCCACAGC
```

FIGURE 3D

```
14201 ATTCAACATT GAAGAAGTTT CTTTCTTAGA GCCCTCATCA TGTGTCTCCT
14251 TGAATCTCAT TGGCCCAAAT TGGTTTAGGC TTGTCCACCC CTGGCAAAGA
14301 GGTAAATTGC CATGAATTGC TTAGATTAAT CACGGGACAG ATGGGATGTT
14351 GGGAAATCAG TCACAATGTC TACTACCTTG GAAAATGCAA AACTCAGACA
14401 TTATGCTGTT GAGAGGGTTG AACAAAGGTC AAAAATAAAT TTTCTGAAGA
14451 CACAAAAATT TACTAAGGGG AAACTGGCTA GGTAA  (SEQ ID NO:3)
```

FEATURES:
Start:    2026
Exon:     2026-2326
Intron:   2327-5804
Exon:     5805-6063
Intron:   6064-6735
Exon:     6736-6899
Intron:   6900-12241
Exon:     12242-12456
Stop:     12457

CHROMOSOME MAP POSITION:
Chromosome 12

ALLELIC VARIANTS (SNPs):
DNA

| Position | Major | Minor | Domain |
|---|---|---|---|
| 811 | G | A | Beyond ORF(5') |
| 1743 | G | C | Beyond ORF(5') |
| 1789 | C | T | Beyond ORF(5') |
| 3633 | C | T | Intron |
| 3750 | A | G | Intron |
| 4355 | T | C | Intron |
| 4496 | C | G | Intron |
| 7581 | G | A | Intron |
| 7802 | A | T | Intron |
| 9362 | A | G | Intron |
| 9437 | G | T | Intron |
| 9461 | G | C | Intron |
| 10740 | G | T | Intron |
| 11194 | A | T | Intron |
| 11619 | A | G | Intron |
| 12173 | T | C | Intron |
| 12683 | G | T | Beyond ORF(3') |

Context:

DNA
Position
811       TGGTTTGCTTTCTACCATTTCCCACCTCCATCCCCTATAAGCTTTAGGTCTGCTCTTTGG
          GGGTGGGTTCATAATCTGGCCCCCTCCCCTACTTTGTTAAGGAACGGCCAAACCCTGCGG
          GGCTTTCCCAGGGTGACACCTGCTTTATGTGATTCCACGCTGGTCAGACTTGGCAAATGG
          TGGATCACAGAGATACATCCTTTGTCCCTTCACACTAGAGAACTTTGTGGTCCCATTTCT
          GTGTCAGACTC
          [G,A]
          CTAAGCCATGAAGGTGTGAGCTAGGACCAGGCTCATCCCAAGGAATGGTGACCCTAGATG
          TTGATCCAAAGAACCACAGAGGCTCCAGCATCATTCCCTGCATCTTATGCAATTCTGGGT
          GTGGCCCCTCACTACTCACACCTCTGGTTTCCTTATTTCCTTTCCTTTACCACCTTACCT
          CTTAGCTTTCTGTAAATTATTTGCTAAATTGCCTAGAATCTCTGTTTCTCCTCCAAGTCC
          CGACCCTGAGAATTTTCTATGTCTCTGGCCCCAGTTCTCTGCTCCTCCTATATCTCATCC 1743      GGTTTGGAAGGTACAGAACCAATGTTGTTTGTTTTACATTAATAAATTTGTCTTGAGTAT
          TTTCCCTGAAAATAAACTTATTTACATACCTGCACTCACGACAAATGATTTTGATCCCTG
          GAGACCAAAATCCCCAGGCTGGGTTGGGGGCAGGGTGGGGACAGGATTTTCTAGGGGAGCT

FIGURE 3E

```
          GTCTGGGGTGAGTCCTCATCTTTCATTTGCCTGCCTTACACCGCCTGGGTGAGCCACCAC
          TCATCACCAACATTACAAGTGGATTATTTCCAATTCTTGGCAGCTTTACCCATCAGGGCA
          [G,C]
          GGGGAGAGAGGGAGGCAGCTACCAGGGCTGTCAGAGGTGACAAGGCTTCAGGTTGGACTT
          GAATTTCTTGCATCTGGGCTAATTGCTGTGGTGATGCATCCACCTATAAAAATTACAGCG
          TGGCTCACCCAGGGACCTAGATTTGTTGCAAGCTGTGGGAGGAAGGAGAGTTCTTCTTCC
          AGGTGGTTTCCTGCAGACTGCCTGCTAGGGCTCAGAGGACCAGCTTCTTCCCTGCTGTCT
          CCTGAGCCCAGTCCCTCTTGGCCATCACATTCCCCTTGCCCTATGGCGGCCCTCACAGAC

1789      TTTGTCTTGAGTATTTTCCCTGAAAATAAACTTATTTACATACCTGCACTCACGACAAAT
          GATTTTGATCCCTGGAGACCAAAATCCCCAGGCTGGGTTGGGGGCAGGGTGGGGACAGGA
          TTTCTAGGGGAGCTGTCTGGGGTGAGTCCTCATCTTTCATTTGCCTGCCTTACACCGCCT
          GGGTGAGCCACCACTCATCACCAACATTACAAGTGGATTATTTCCAATTCTTGGCAGCTT
          TACCCATCAGGGCAGGGGGAGAGAGGGAGGCAGCTACCAGGGCTGTCAGAGGTGACAAGG
          [C,T]
          TTCAGGTTGGACTTGAATTTCTTGCATCTGGGCTAATTGCTGTGGTGATGCATCCACCTA
          TAAAAATTACAGCGTGGCTCACCCAGGGACCTAGATTTGTTGCAAGCTGTGGGAGGAAGG
          AGAGTTCTTCTTCCAGGTGGTTTCCTGCAGACTGCCTGCTAGGGCTCAGAGGACCAGCTT
          CTTCCCTGCTGTCTCCTGAGCCCAGTCCCTCTTGGCCATCACATTCCCCTTGCCCTATGG
          CGGCCCTCACAGACCTCTCATTTATGTATCGCTGGTTCAAGAACTGCAATCTGGTTGGCA

3633      GAACTAGTCTGGAGCCCATGCGCAGGTCAGGGCAACAGAGCCCTGGAGCCAGGGGGATCT
          AGACAGTAACTCCCTGCTTGATTCTTCTCCTTAGCACTTATCACTAGTCAATGTACAATA
          GATTTTACTTATTTATTGTCTGTTTCCTCTGCTAGAATAAAGCTTCCTGGGGACAAGGAT
          TTTTGTCCCTTTTATTTACTGTACATCCTTAGTACCTAGAATAATGTCTGGCACCTAGTA
          AGGTACTGAATAAATAGATTTGAGTGAGCTAATTAATTAATAATTCAGCAAGAGTGAGCC
          [C,T]
          CTGTCTTCAGCAGGCTGTCTCAGCCAGTTCCCTACATTCAGCCTTGAGCCACTTGCCTTA
          ATACCTCACTTAGCATGTGAGTTTCCTGTTGCTATTGTAACAAATAACACAACTGTGGGG
          GTCTGAAGACAATACAAACATATTATCTTGTAGTTGTGGAGGAGTAATGTCTAAAATAGG
          CCTCACTGATCTAAAATCAAAGTCAGCAGAGCTGTGTTCCTTCTAGAGGCTGTAGAGGAG
          AATCCGTCTCATCGACTTTTCCAGCTTCCAGAGGCAGCTGGCATCCCCTGGCTCCTGGCC

3750      ATAGATTTTACTTATTTATTGTCTGTTTCCTCTGCTAGAATAAAGCTTCCTGGGGACAAG
          GATTTTTGTCCCTTTTATTTACTGTACATCCTTAGTACCTAGAATAATGTCTGGCACCTA
          GTAAGGTACTGAATAAATAGATTTGAGTGAGCTAATTAATTAATAATTCAGCAAGAGTGA
          GCCCTCTGTCTTCAGCAGGCTGTCTCAGCCAGTTCCCTACATTCAGCCTTGAGCCACTTGC
          CTTAATACCTCACTTAGCATGTGAGTTTCCTGTTGCTATTGTAACAAATAACACAACTGT
          [A,G]
          GGGGTCTGAAGACAATACAAACATATTATCTTGTAGTTGTGGAGGAGTAATGTCTAAAAT
          AGGCCTCACTGATCTAAAATCAAAGTCAGCAGAGCTGTGTTCCTTCTAGAGGCTGTAGAG
          GAGAATCCGTCTCATCGACTTTTCCAGCTTCCAGAGGCAGCTGGCATCCCCTGGCTCCTG
          GCCTGCTACCTCCATCTTCAAGGCCCGCAAGGTTGGGCCCAGTCTTTTTCACACTTTTCT
          CAAGCTCTCTGATTCTCCGGTTTCTGCCTCTTTCCACTTAGGACTTGTGATTATATTGGG

4355      CCAGGTTAATCCAGGATAATTTCCCTGTGTTAGCTTCCTCCCTAACTTTAAGGACAATTA
          ATTAGCAACCTCCATTCCACCTGCAACCTTAATTCCCCTTTCCCATGTAATCCAGCAGAT
          TCACAGGTTCCAGAGATAATGAGGATGGGGACATCTTTGGGGGACCATTATTTTGCCTAA
          GCCACTTGGCAATATCCTGGTCTAAGAAACACTGGGAACTGGGGTGGGTAGGGGGATGGG
          AGAGGAAGTTCTTTCATGCTTTCTCATTGCTCCTGAATGGAGAAAGGCAGGGAGACTGGG
          [T,C]
          AGGGGCATGGCTTGGGTGGGGACCCCAGCCCTAGAGGGAGGGGTGGACTAGGATTTATGT
          TTGTGTTGAGACCTGCCCTCAGGAGACAGTGGGATGCGCCTGCAGAGTATCTTGGGGCTG
          CTGAGGCTGGGGCTGTGGTGCGAATCACCAGGCAGTAGGACTTGGGGAATCCTTGCATGA
          AGGAGCTGGAAGGGGTCCTTGAGGGAGTGTTTAGAGGGGTTTACAGTAGAACCCCAATATG
          TAAAACAAATGAAAGGAGAGCTTCTCCTGCATTTTCCTCCCCCTAGAAGGCTTGCAAAAT

4496      AGGATGGGGACATCTTTGGGGGACCATTATTTTGCCTAAGCCACTTGGCAATATCCTGGT
          CTAAGAAACACTGGGAACTGGGGTGGGTAGGGGGATGGGAGAGGAAGTTCTTTCATGCTT
          TCTCATTGCTCCTGAATGGAGAAAGGCAGGGAGACTGGGAGGGGCATGGCTTGGGTGGGG
          GACCCCAGCCCTAGAGGGAGGGGTGGACTAGGATTTATGTTTGTGTTGAGACCTGCCCTC
          AGGAGACAGTGGGATGCGCCTGCAGAGTATCTTGGGGCTGCTGAGGCTGGGGCTGTGGTG
          [C,G]
          GAATCACCAGGCAGTAGGACTTGGGGAATCCTTGCATGAAGGAGCTGGAAGGGGTCCTTG
          AGGAGTGTTTAGAGGGGTTTACAGTAGAACCCCAATATGTAAAACAAATGAAAGGAGAGC
          TTCTCCTGCATTTTCCTCCCCCTAGAAGGCTTGCAAAATACAGCCTGGAAACAACTGTTT
          TAGTCTAATCTGATGAAGAGCCTGAGGCCCAGAGAGGGAAGTGACTTGTTCAAGGCTGGA
          GGTAAAACCAGGACTGGACCTGAAGCTCTTCAACCCTGGGCCCCTGCAGAGTTGAATGAC

7581      TTTCCCATGCCTCAGTTTTCTTATTTACAAAATGGAGCTAAAGATAGTGCCTCCCTCATG
          GGGTTGTTATGAGGGTTAGTATGTGTGAAGTACTTTGCACATTCTGAGTGCTTGTTAATA
```

FIGURE 3F

```
         AAGAAGAAAATGAGCACATGGGGATTTAAAAGGGAGGGTCTCTAGGCAACTCTCTTTCTT
         TCCCTGAGCTGAGGGTCTCCTGTGAATCATAGGTGTTTTTGGAGGGTAGAGGTGGGACAC
         GGCAGCTGTTTACCCTGCTGCCCCAAAACTTTCTGCCACGAAAGTTGTCTGCTGGATGTC
         [G,A]
         TACGTCAACAGAGCACAAAGCCAAGTCAGCCATTTTTTTCACTTAATACATACACACTTT
         ATTGCATTTTTGTTTTTTGTTTTTGTTTTGAATCAGTAATACAAAGCATGCAAGGCTGCC
         ATGTCCCAAGCCTGTGTGGGGCTGGAGAGCTGGAGCGGACACAGCAGTATGCCTGCCCTT
         CACTGCCTGTAGCTTATGGCCCAGTAGGGGAGACAAACATAAATCAAAACACATGTGTTT
         ATGGTAGATGTGGATAAGTGCTACAGAGGAGAAACAGGGTTGTGAAAGAAGAATGGAGCA

7802     GAGGGTAGAGGTGGGACACGGCAGCTGTTTACCCTGCTGCCCCAAAACTTTCTGCCACGA
         AAGTTGTCTGCTGGATGTCGTACGTCAACAGAGCACAAAGCCAAGTCAGCCATTTTTTTC
         ACTTAATACATACACACTTTATTGCATTTTTGTTTTTTGTTTTTGTTTTGAATCAGTAAT
         ACAAAGCATGCAAGGCTGCCATGTCCCAAGCCTGTGTGGGGCTGGAGAGCTGGAGCGGAC
         ACAGCAGTATGCCTGCCCTTCACTGCCTGTAGCTTATGGCCCAGTAGGGGAGACAAACAT
         [A,T]
         AATCAAAACACATGTGTTTATGGTAGATGTGGATAAGTGCTACAGAGGAGAAACAGGGTT
         GTGAAAGAAGAATGGAGCAGGAAGTTGCGGTCCCAATTCAGACTATGGTGAAGGGGAGAG
         CTTCTGAGTTGACTTTGAGGAGGAATAAGAGTTAGGTGTTGCTGGGAAGGGGAAAGAGGG
         GATGCGTAGGGACTTTTTTTCTGCAGGAAGGCTCTGAGGCAGAAAACTCCATTTGAGGAA
         CTTTAAAGAAACCAGCAGGTGGGAAGCAATGGGAGGTAGCTGGGGTATACGGAATAAATT

9362     AACTCCTCCGAAAACCTTGTCCAAAAGCTAGTATTGTACTAAAGAATAGTAAGGATTGGG
         TTTATAAAATATCTTAGGCCAATTCACCTGTAGTCCACACCATAATTTCAGAGGAAAATT
         TTCAGGCAGTGGTCAACTACATTTAGATAAACGTTTTCCCAAGTGGTTATACTAGAATTT
         TTGCTTCAGTTGCCCAGTGTTTATTGGGATTCAGAGATGAGACACTCTCCAGGAAACTAG
         CAGGGAAGATGTGAAAGCAAATACACCACCACATGAAGAATCTTGCTATAATGGACATGC
         [A,G]
         TACAAAACAAAGCAGCAATGCAGACTTCATTCTGCTGTCACAGAAGCCTTACAGAGGTGA
         CAGTTAATGCCTTAGTGAGTTTTGAAGGATGAATAGGAGTACACCAAAAGGGAAAGAGAT
         GGCGGATGTTTCACACAAGAGGAAGGGTGTGAGCAACGTTTTAGTGACCTGACATAGCAT
         TGTATGCTTTTGGAGGCAGTGCAGATTCAGGCTTGTATTCCAGCAGTCCCTCTAATCATG
         TTGTATAGCTCTCCAAACTTGTTTATCCATTTATAAAGTACAATTCCTCTCTCATGGATT

9437     AGGCCAATTCACCTGTAGTCCACACCATAATTTCAGAGGAAAATTTTCAGGCAGTGGTCA
         ACTACATTTAGATAAACGTTTTCCCAAGTGGTTATACTAGAATTTTTGCTTCAGTTGCCC
         AGTGTTTATTGGGATTCAGAGATGAGACACTCTCCAGGAAACTAGCAGGGAAGATGTGAA
         AGCAAATACACCACCACATGAAGAATCTTGCTATAATGGACATGCATACAAAACAAAGCA
         GCAATGCAGACTTCATTCTGCTGTCACAGAAGCCTTACAGAGGTGACAGTTAATGCCTTA
         [G,T]
         TGAGTTTTGAAGGATGAATAGGAGTACACCAAAAGGGAAAGAGATGGCGGATGTTTCACA
         CAAGAGGAAGGGTGTGAGCAACGTTTTAGTGACCTGACATAGCATTGTATGCTTTTGGAG
         GCAGTGCAGATTCAGGCTTGTATTCCAGCAGTCCCTCTAATCATGTTGTATAGCTCTCCA
         AACTTGTTTATCCATTTATAAAGTACAATTCCTCTCTCATGGATTGTTAGGAGAATTAAA
         CAGAAATGCAAAGTACTCAGCTCTGCTACAGTAAGAGCTGAACAAACCTTTGCCATTGCC

9461     CCATAATTTCAGAGGAAAATTTTCAGGCAGTGGTCAACTACATTTAGATAAACGTTTTCC
         CAAGTGGTTATACTAGAATTTTTGCTTCAGTTGCCCAGTGTTTATTGGGATTCAGAGATG
         AGACACTCTCCAGGAAACTAGCAGGGAAGATGTGAAAGCAAATACACCACCACATGAAGA
         ATCTTGCTATAATGGACATGCATACAAAACAAAGCAGCAATGCAGACTTCATTCTGCTGT
         CACAGAAGCCTTACAGAGGTGACAGTTAATGCCTTAGTGAGTTTTGAAGGATGAATAGGA
         [G,C]
         TACACCAAAAGGGAAAGAGATGGCGGATGTTTCACACAAGAGGAAGGGTGTGAGCAACGT
         TTTAGTGACCTGACATAGCATTGTATGCTTTTGGAGGCAGTGCAGATTCAGGCTTGTATT
         CCAGCAGTCCCTCTAATCATGTTGTATAGCTCTCCAAACTTGTTTATCCATTTATAAAGT
         ACAATTCCTCTCTCATGGATTGTTAGGAGAATTAAACAGAAATGCAAAGTACTCAGCTCT
         GCTACAGTAAGAGCTGAACAAACCTTTGCCATTGCCATTATAGTCTGGCAGGAGTGCTGT

10740    CCATGTCAGCTTGCTCCACATCCTCAGCCCACAAAGCTTTCCCTGGCGCCGAGGGGGCAG
         AGAGAGCCTCCTGGGCATCCTGAACGATTCCTTCGACCCTCAGCCCTGCTGCTGGTGGCC
         TCTGTGCCAGCTCTACGGTCAGAGGTCAGGGTGTGGCTTCCTAAGACATTACTGCTTTAT
         GGACAGTCTGGCTTTGAGTTAGTGTGGCTCTTGTTGAGATCCCAAAATATAGTTTGGCTT
         TTCCCCTGCATCAGTTTTCTTTCCAGGAAACAGAAAATGGAGTTTCTCGGAGTCTGGGGT
         [G,T]
         AAGGGGACTGAAGTGATGCTGCCCCATTCTCACCAACCACCCACAAGGGTCCTGGCCCCA
         AGCGGGTGAATTCCTTGCCTGCCTGGACCATTCTCAAAGTCAGGGCAGCTTTGGCTTCCT
         CTCCATTTTCAAGTTTTTCATACCTTATCAGGGCAGTCTGACTTTGAAGCATCATTTTCCC
         TGGAGTCCTCAGGGCTCTCAATGAAGCATGAATCCCCCTGTCCTGGGGTGAGGATGCAGA
         TGAGGGCCTGGTGGGTGTGTGGTGTGGCCCTTCTCCCATTTATGTCATGAACTTTGGCAG

11194    AGTCTGACTTTGAAGCATCATTTTTCCCTGGAGTCCTCAGGGCTCTCAATGAAGCATGAAT
```

FIGURE 3G

```
        CCCCCTGTCCTGGGGTGAGGATGCAGATGAGGGCCTGGTGGGTGTGTGGTGTGGCCCTTC
        TCCCATTTATGTCATGAACTTTGGCAGACTTGTACTATTTGGGTGCTCTGTCCCCATCTC
        CACCCCTGTGGGTCAATGCAAACAGAACAACTCCTCACATTTGTGAGGGCCCCACGAGGT
        GCTTGTCTATGCCTTAGATTATTTGAGTGACAGTGGCCTTATGACTGAGGTAGGGGCAGT
        [A,T]
        TTACTATTTTTAAATAATATTTTCTCCTGCATGTTTTTGTTTAAATGTGGGAACTCTAGG
        AAGTACATAGAAGAAAAAAAAAAAGGGCTGTTTTCCCATCATGTTTGCTCTTCTGTACTCC
        CCCAGTGTCTACCCTGCTGTTAATCATCTTTGTTATTCTCCAGGACAGATATTTTTTGAG
        ATGGAGTCTCACTCTGTTGCCCAGGCTGGAATGCAGTGGCGCGATCTTGGGTCACTGCAA
        CCTCCCACTCCTGAGTTCAAGTGATTGTCATGCCTCAGCCTCCTGAGTAGCTGCGATTAT

11619   GTGTCTACCCTGCTGTTAATCATCTTTGTTATTCTCCAGGACAGATATTTTTTGAGATGG
        AGTCTCACTCTGTTGCCCAGGCTGGAATGCAGTGGCGATCTTGGGTCACTGCAACCTC
        CCACTCCTGAGTTCAAGTGATTGTCATGCCTCAGCCTCCTGAGTAGCTGCGATTATAGGC
        ACGCGCCACCACGCTCACCTAATTTTTGTATTTTTAGTAGAGACAAGGTGTCACCATGTT
        GGCCAGGCTGGTCTCAAACTCCTGACCTCAGGTGATTGGCCTGGCTTGGCATCCCAAAGT
        [A,G]
        CTGGGATTACAGGCCTGAGCCACTATGCCCAAACTTTAGGAAAGATAGTATTATCTCCAT
        TTTATAGACAATAAAAGTTTAAGCTCAAAGTCATATAACTAATAAGCGGCACAGTTATAA
        GGAGAATGTGCACAGTTCTTCTCATCACCAGTCTAATGCAATAGTAGGACTTCAATGCAC
        AATTGTTGAATTCAGAAAGATAAATAAGACTATTTGTTTATTTATTTATTTATTTATTTA
        TTTTGAGACAGCGTGTCATTCTGTTTCCCAGGCTGGAGTGCAGTGGTGTGACCTCGGCTT

12173   TGTCATTCTGTTTCCCAGGCTGGAGTGCAGTGGTGTGACCTCGGCTTACTGAAACCTCAG
        CCTCCTGGGTTCAAGTGGTTCCCATACCTCAGCCTCCCGAGTAGCTGGGATTACAGGCAT
        GTGCCACCAAGCCCAGCTGATTTTTATATTTTTAGTAGAGATGGGGTTTCACCATGTTGG
        CCAGGCTAAGATTATTTATAATAGTCTTATAAATGTGTGTTTGTATAAGGGACCACCTGG
        AGGGTGTGGCGGACCTGCCTGAAATGTTAGATCAGGGATCTGATGGAAAGGGAACTTGGA
        [T,C]
        GGAATTCGGAAGAAGCCATCTTTTATGAAGAATAACAGAGCCTTTTTCCCCTCTCTGCCC
        TCAAACAGATACTGACAAGTTAAAAAACATAATGCAGGTGGCAGAGCCCAGAGTCAGAGA
        TGTCATCAACAGCATGGAGCATGCTATTGTTTCCCGGAGCCCTCGCATCCGCTACAACCC
        TGGCCTGATGCCAAACTCCTCTACATCCCTCTGGCTAAGTTGCCCACCCCTGTGACAGA
        TTTCATCCTAAGCCGGTACCTTCCAAGGCCAGCGGACAGTGTCTAAACTGGGGAGGATCA

12683   CTCTGGCTAAGTTGCCCACCCCTGTGACAGATTTCATCCTAAGCCGGTACCTTCCAAGGC
        CAGCGGACAGTGTCTAAACTGGGGAGGATCAATGGGTCAGTGGAGCCTAGAAGTGGGGGA
        GGAAGGAAGGACCGTGGGGTCACAAAAGGTGGTATCGGTTATCCTGGGGGCATTGGCTGC
        AAAGGAAGCTTGGCTCAGCTGACACCCACTGCTGTCGAATTTACCAGTAACTTCTAACAG
        AAGGTGAATGCCTCTTCCCACCCTCTGGGACCCCACAGAAACCTGAGGTGGTCTTTGCAG
        [G,T]
        TTCAGCGATCTGCAGCAATAGCTCCAAGGACGTCTGTCACCCAATCAGGATACAGCTTTT
        TCTGGTCCTGGAAAAGTCATGGAGAAGAAAACCAGCTCCTGTGGAATCATGAGCCCCTTT
        CAGTTATCACTGCCACTGAGAAATACTGTGGGATAATCTTGCCTCCAGGAGAATCTAACC
        ACCTTCCTAATGGGTCCCTCAATATGCATAACTTCATTCACATAACCCATTACTGAAGTA
        TGCGGTAGGGCAGATAGGGAGTGCAAGATTAAATCAGACAAAAGTTTAAAATATTTTCTT
```

FIGURE 3H

US 6,900,040 B2

SEQUENCE LISTING

<160> NUMBER OF SEQ ID NOS: 4

<210> SEQ ID NO 1
<211> LENGTH: 993
<212> TYPE: DNA
<213> ORGANISM: Homo sapiens

<400> SEQUENCE: 1

```
ttggccatca cattcccctt gccctatggc ggccctcaca gacctctcat ttatgtatcg      60
ctggttcaag aactgcaatc tggttggcag cctctcagag aagtacgtct tcatcacagg     120
ctgtgactct ggcttcggga acctgctggc caaacagctg gttgatcggg gcatgcaggt     180
gctggctgct tgcttcactg aggagggatc ccagaaactt cagcgggata cctcctatcg     240
gctgcagacc accctactgg atgtcaccaa gagcgaaagc atcaaggcgg cggcccagtg     300
ggtgagggac aaagtgggcg aacaaggcct ctgggccctg gtgaacaatg ctggtgtggg     360
cctgcccagt ggtcccaacg aatggctgac caaggatgac tttgtgaagg tgattaatgt     420
gaacctggtg ggactgatcg aagtgaccct tcacatgctg cccatggtca agagagcccg     480
gggcagggtt gtcaacatgt ccagctctgg tggtcgtgtg gctgtcattg gtggtggcta     540
ctgcgtctcc aagtttggcg ttgaggcctt ctctgacagc ataaggcgtg agctctacta     600
ctttggggtg aaagtctgca tcattgagcc agggaactat cggacagcca ttctcggcaa     660
ggagaacctg gagtcacgca tgcgaaagct tgggagagg ctgcctcagg agacccggga     720
cagctacgga gaggattatt tccgcgtcta tactgacaag ttaaaaaaca taatgcaggt     780
ggcagagccc agagtcagag atgtcatcaa cagcatggag catgctattg ttttcccggag    840
ccctcgcatc cgctacaacc ctggcctgga tgccaaactc ctctacatcc ctctggctaa     900
gttgcccacc cctgtgacag atttcatcct aagccggtac cttccaaggc cagcggacag     960
tgtctaaact ggggaggatc aatgggtcag tgg                                  993
```

<210> SEQ ID NO 2
<211> LENGTH: 313
<212> TYPE: PRT
<213> ORGANISM: Homo sapiens

<400> SEQUENCE: 2

```
Met Ala Ala Leu Thr Asp Leu Ser Phe Met Tyr Arg Trp Phe Lys Asn
  1               5                  10                  15

Cys Asn Leu Val Gly Ser Leu Ser Glu Lys Tyr Val Phe Ile Thr Gly
             20                  25                  30

Cys Asp Ser Gly Phe Gly Asn Leu Leu Ala Lys Gln Leu Val Asp Arg
         35                  40                  45

Gly Met Gln Val Leu Ala Ala Cys Phe Thr Glu Glu Gly Ser Gln Lys
     50                  55                  60

Leu Gln Arg Asp Thr Ser Tyr Arg Leu Gln Thr Thr Leu Leu Asp Val
 65                  70                  75                  80

Thr Lys Ser Glu Ser Ile Lys Ala Ala Ala Gln Trp Val Arg Asp Lys
                 85                  90                  95

Val Gly Glu Gln Gly Leu Trp Ala Leu Val Asn Asn Ala Gly Val Gly
            100                 105                 110

Leu Pro Ser Gly Pro Asn Glu Trp Leu Thr Lys Asp Asp Phe Val Lys
        115                 120                 125

Val Ile Asn Val Asn Leu Val Gly Leu Ile Glu Val Thr Leu His Met
```

```
                  130                 135                 140
Leu Pro Met Val Lys Arg Ala Arg Gly Arg Val Asn Met Ser Ser
145                 150                 155                 160

Ser Gly Gly Arg Val Ala Val Ile Gly Gly Tyr Cys Val Ser Lys
                165                 170                 175

Phe Gly Val Glu Ala Phe Ser Asp Ser Ile Arg Arg Glu Leu Tyr Tyr
            180                 185                 190

Phe Gly Val Lys Val Cys Ile Ile Glu Pro Gly Asn Tyr Arg Thr Ala
            195                 200                 205

Ile Leu Gly Lys Glu Asn Leu Glu Ser Arg Met Arg Lys Leu Trp Glu
210                 215                 220

Arg Leu Pro Gln Glu Thr Arg Asp Ser Tyr Gly Glu Asp Tyr Phe Arg
225                 230                 235                 240

Val Tyr Thr Asp Lys Leu Lys Asn Ile Met Gln Val Ala Glu Pro Arg
                245                 250                 255

Val Arg Asp Val Ile Asn Ser Met Glu His Ala Ile Val Ser Arg Ser
                260                 265                 270

Pro Arg Ile Arg Tyr Asn Pro Gly Leu Asp Ala Lys Leu Leu Tyr Ile
            275                 280                 285

Pro Leu Ala Lys Leu Pro Thr Pro Val Thr Asp Phe Ile Leu Ser Arg
        290                 295                 300

Tyr Leu Pro Arg Pro Ala Asp Ser Val
305                 310

<210> SEQ ID NO 3
<211> LENGTH: 14485
<212> TYPE: DNA
<213> ORGANISM: Homo sapiens

<400> SEQUENCE: 3
cctcagcagt ctatgctctc ccactggagg gaaatggcct ggcagaggag agggctcctc      60
tcctctgaga tacctgtgtg catggggtgg ggatggggag tgcagctacc aacctgacct     120
atcagacctt aggggccagc ttggcaagga atgctgtcat ctgagagagg gaggcatttc     180
tagccctggg aagaagagcc ttctatgtgg tcctacctcc ctcacacccc ccaccctcat     240
ggactgtgtg tttagtttga ggccagggga acactgccag catagaggcc caggaggtgc     300
tgagtcaggc ccaggcctgt gctggggcag ttctgagtta tccttatgct aagtcagacc     360
caactcctgg acctcacctg tgtcctcaag gactgggata cccaatgccc ggacctgct     420
cagtcttgag tgacatggtc tgacctgttt cagccaagac ttctctgttc attcacccag     480
gaggcagaca gagactggga gattgttccc agatcccgca taggaggtgc tctgcctcgg     540
gttggttatg aagtaggtgt ggtttgcttt ctaccatttc ccacctccat cccctataag     600
ctttaggtct gctctttggg ggtgggttca taatctggcc ccctccccta ctttgttaag     660
gaacggccaa accctgcggg gctttcccag ggtgacacct gctttatgtg attccacgct     720
ggtcagactt ggcaaatggt ggatcacaga gatacatcct ttgtcccttc acactagaga     780
actttgtggt cccatttctg tgtcagactc gctaagccat gaaggtgtga gctaggacca     840
ggctcatccc aaggaatggt gaccctagat gttgatccaa agaaccacag aggctccagc     900
atcattccct gcatcttatg caattctggg tgtggcccct cactactcac acctctggtt     960
tccttatttc ctttccttta ccaccttacc tcttagcttt ctgtaaatta tttgctaaat    1020
tgcctagaat ctctgtttct cctccaagtc ccgaccctga gaattttcta tgtctctggc    1080
```

-continued

```
cccagttctc tgctcctcct atatctcatc ccctcttaca gtcaaggcct ctgcccagac   1140
aattccctca gctgcccagt gaactcatga tccctcctca tcatcttgcc cagggctgct   1200
tactggtgac ctgagtatga cccccacagg gtgtcaggcc tgagtccccc aggtctttct   1260
gctttctggt ggctaagctt cacatgccag cctcccctat aggagggccc tgctgcctct   1320
agcctcagga caatggaggt catccaccc taggagaaat ccattgcttt tcatcctctc   1380
tcatgatgga gacttaccta agaattccag agagctgatg acctgcgact tgtttctctt   1440
ggggtttgga aggtacagaa ccaatgttgt ttgttttaca ttaataaatt tgtcttgagt   1500
attttccctg aaaataaact tatttacata cctgcactca cgacaaatga ttttgatccc   1560
tggagaccaa atccccagg ctgggttggg ggcagggtgg ggacaggatt tctaggggag    1620
ctgtctgggg tgagtcctca tctttcattt gcctgcctta ccgcctggg gtgagccacc   1680
actcatcacc aacattacaa gtggattatt tccaattctt ggcagcttta cccatcaggg   1740
caggggagag gagggaggca gctaccaggg ctgtcagagg tgacaaggct tcaggttgga   1800
cttgaatttc ttgcatctgg gctaattgct gtggtgatgc atccacctat aaaaattaca   1860
gcgtggctca cccagggacc tagatttgtt gcaagctgtg ggaggaagga gagttcttct   1920
tccaggtggt ttcctgcaga ctgcctgcta gggctcagag gaccagcttc ttccctgctg   1980
tctcctgagc ccagtccctc ttggccatca cattccccct tgccctatgg ggccctcaca   2040
gacctctcat ttatgtatcg ctggttcaag aactgcaatc tggttggcaa cctctcagag   2100
aagtacgtct tcatcacagg ctgtgactct ggcttcggga acctgctggc caaacagctg   2160
gttgatcggg gcatgcaggt gctggctgct tgcttcactg aggagggatc ccagaaactt   2220
cagcgggata cctcctatcg gctgcagacc accctactgg atgtcaccaa gagcgaaagc   2280
atcaaggcgg cggcccagtg ggtgagggac aaagtgggcg aacaaggtgg ggcgaattac   2340
attctttggc tttcttggtt tctccttctt cctcttcctc tctcccgaag catctgacag   2400
tatcagagac cctgatgtcc agattgggtg ggagggtga tgtagggaaa ggcccctgcc   2460
tcaatctgat tggaagccac tgcatggttt ggcctgttca catgaagggg tgatttccca   2520
aggaagtttt ctgtcctgga aactcagaga acgggaaag aggtctcaat aggaagcgag   2580
ggggaagat gtgttctgtg tgtccaaacc tctaaaaatg gacgtgcctg gctgggcgtg   2640
gtggctcacg cctatgagcc cagcactttg gaaggccgaa gtgggaggat catgaggtca   2700
agagatcgag accatcccgg ccaacatggt gaaaccccat ctctactaaa aagtataaaa   2760
attacctggg tgtggtggca cgtgcctgta gtcccagcta ctcaggaggc tgaggcagga   2820
gaatcacttg aacccgggag gcggaggttg cagtgagcca agattgcgcc actgcactcc   2880
agcctcgtga cagagcaaga atccctctca aaaagaaaaa aaagaaaaaa aaggatgtg    2940
cctctctgat gtttcagcag tcctaaccat cagctcctgg ggaaatacaa acacatttct   3000
tgttgggatc aggatggggg aggggaatg agacaggagg ctggatccca tgagtgggtg   3060
cagtttgtct ccttgactat gtcaggcagg ggagaaagag atctggtctc ttcttgacat   3120
catggtgggt gttgatttga cttcagggca agtatgtatg tcacagtggc tgctcctatt   3180
gggaaaggaa gctgtggact ggggctggcc caggactgtg tggggacctg cctcatgcac   3240
ttccagcaca cagggtgtgg gcccaggaac aggaggaaca ggatggctga gttgcagaag   3300
cagcagacta gaggaagtcc tccctcctaa aggaactagt ctggagccca tgcgcaggtc   3360
agggcaacag agccctggag ccaggggat ctagacagta actccctgct tgattcttct   3420
ccttagcact tatcactagt caatgtacaa tagatttac ttatttattg tctgtttcct    3480
```

-continued

```
ctgctagaat aaagcttcct ggggacaagg attttttgtcc cttttattta ctgtacatcc    3540
ttagtaccta gaataatgtc tggcacctag taaggtactg aataaataga tttgagtgag    3600
ctaattaatt aataattcag caagagtgag cctctgtctt cagcaggctg tctcagccag    3660
ttccctacat tcagccttga gccacttgcc ttaatacctc acttagcatg tgagtttcct    3720
gttgctattg taacaaataa cacaactgtg ggggtctgaa gacaatacaa acatatattatc    3780
ttgtagttgt ggaggagtaa tgtctaaaat aggcctcact gatctaaaat caaagtcagc    3840
agagctgtgt tccttctaga ggctgtagag gagaatccgt ctcatcgact tttccagctt    3900
ccagaggcag ctggcatccc ctggctcctg gcctgctacc tccatcttca aggcccgcaa    3960
ggttgggccc agtcttttttc acactttttct caagctctct gattctccgg tttctgcctc    4020
tttccactta ggacttgtga ttatattggg ctcaccaggt taatccagga taatttccct    4080
gtgttagctt cctccctaac tttaaggaca attaattagc aacctccatt ccacctgcaa    4140
ccttaattcc cctttcccat gtaatccagc agattcacag gttccagaga taatgaggat    4200
ggggacatct ttggggggacc attattttttgc ctaagccact tggcaatatc ctggtctaag    4260
aaacactggg aactggggtg ggtaggggga tgggagagga agttctttca tgctttctca    4320
ttgctcctga atggagaaag gcagggagac tgggtagggg catggcttgg gtggggaccc    4380
cagccctaga gggaggggtg gactaggatt tatgtttgtg ttgagacctg ccctcaggag    4440
acagtgggat gcgcctgcag agtatcttgg ggctgctgag gctggggctg tggtgcgaat    4500
caccaggcag taggacttgg ggaatccttg catgaaggag ctggaagggg tccttgagga    4560
gtgtttagag gggtttacag tagaacccca atatgtaaaa caaatgaaag gagagcttct    4620
cctgcatttt cctcccccta gaaggcttgc aaaatacagc ctgaaacaa ctgttttagt    4680
ctaatctgat gaagagcctg aggcccagag agggaagtga cttgttcaag gctggaggta    4740
aaaccaggac tggacctgaa gctcttcaac cctgggcccc tgcagagttg aatgacaaca    4800
cttagcatta tttctttcca tttgtaccaa cctaattgaa atatctcaag gatagtcctc    4860
atcacatttt ccataattat tttatttaaa tattttatat atttatttat aaatattatt    4920
atttccttct aggcttgtga gttccttgag ggataagatg ctgtgttgtt cattttatgt    4980
ctcctttgcc ctgtattttta ctttatttta ttttatatcg ttttatttca ttttattttt    5040
agagacagag tctcactctg tcacccaggc tggagtgcaa tggcaccatt atagctcact    5100
gtaacctcga acaaggtaac ctgtaacccg ggctcaagtg attctcccac ctcagcctcc    5160
caagtagcta gaactacagg cacataccac cacgcctgac taatttttttt tcttttttttg    5220
tagagacagg gtcttactc tgttgctcag gctggtctca aactcctggc tcaagtgat    5280
cctcccacct cagcctctca aagggttgtg attacaagtg tgagtcactg cacctggcct    5340
ccttcaccct gtaattgtca cagactagat aaatgcatga ataaatgtgt gaagatgaat    5400
gaatgaatgg attgattttg gtagtatgtg aaatgcagtt ggttatactt aagtgaatag    5460
agagggagaa gtatgatggg gaagggatct aaacattaat tcattggtat gaaaatgaaa    5520
ctcttatccc aaagctgata gctgaaatgc tgtcacctaa cacctcgatt gtagctagta    5580
cagagcgcca gctagccggc agactttatg tgaatcagga aaaagtgtcc cttcagggaa    5640
aacgagttag taaaagacac accttccttt tatgttatag cctgaccgag ttatgtcttg    5700
tgcacctgct caaccatcct tgagggcact gagccggtgg ggagcagaac ttggttcttt    5760
cccaggccca ctgatgattt ctgtgtggtt catctcaccc ccaggcctct gggccctggt    5820
```

-continued

```
gaacaatgct ggtgtgggcc tgcccagtgg tcccaacgaa tggctgacca aggatgactt    5880
tgtgaaggtg attaatgtga acctggtggg actgatcgag gtgacccttc acatgctgcc    5940
catggtcaag agagcccggg gcagggttgt caacatgtcc agctctggtg gtcgtgtggc    6000
tgtcattggt ggtggctact gcgtctccaa gtttggcgtt gaggccttct ctgacagcat    6060
aaggtaactg ggccctggta ctgaacaatt ctgggtgaaa atcccagaga ttagagaggg    6120
ttgggagtga cagcatgtgg gcaggggaat ccgcagaca ggaagctaac acaatagcag     6180
aaggaaggtt agacctcaag gtgctttctc caaggaccaa gagcagggat gaggagaaga    6240
ggtagggtgg aaatacaagg catcaggtgg gccttcccctt gagcggcacc aggtgagtg    6300 aaaccctgtt tgggcctgtg agaggaggga gagtccccca aacagacaga caggcctgga    6360
ggcacaggtc ccctctggga ggtccttaga ggagcgtgca ggccttgtgt atatccacac    6420
cattcaccgt gtgggtgttg agtgaggggt tgctaatggg agggacctgg tgggaggcaa    6480
ggctttggcc tagattctct attgacttct tcccgctggt tgtgcctaat gcaaattgcc    6540
cagagactgc tgggccagtt ttggaaaggg ctgagtccct aaggaagggc ttatttgcac    6600
aaaggcaatg ccagggccaa gtacaggggt gagagaagca tctctaggtt cctgaaagac    6660
cagcccatcc agaggtgact ctccgtgatg attgtcatct tggggcccag actgactgca    6720
actcttcttt cccaggcgtg agctctacta ctttggggtg aaagtctgca tcattgagcc    6780
agggaactat cggacagcca ttctcggcaa ggagaacctg gagtcacgca tgcgaaagct    6840
ttgggagagg ctgcctcagg agacccggga cagctacgga gaggattatt ccgcatctg    6900 taagttcctg gggcaggaga ggggtctctg aggggggcga gtgggtcttg gggtcattag    6960
ctggctttcc gtttacagat ggtgagacaa aatgcagagg agttcaggac ccaaggtcac    7020
atagtggcac agctggggtt tgagaataga gagcaagtgg cagaatcatc acttctggag    7080
cagcccgggg agttaagggc aattcagccc actcctggca cctgccccca cagcatcatg    7140
atgcagggga atcaggtgaa aatgcactga gataaataca gcaaagagat caagggcatg    7200
gctgctggag ccggactgcc tgggttcaaa tcctggctct actacttacc agctaggaga    7260 cttggacct attacctagt tttcccatgc ctcagttttc ttatttacaa aatggagcta    7320
aagatagtgc ctccctcatg gggttgttat gagggttagt atgtgtgaag tactttgcac    7380
attctgagtg cttgttaata aagaagaaaa tgagcacatg gggatttaaa agggagggtc    7440
tctaggcaac tctctttctt tccctgagct gagggtctcc tgtgaatcat aggtgttttt    7500
ggagggtaga ggtgggacac ggcagctgtt taccctgctg ccccaaaact ttctgccacg    7560
aaagttgtct gctggatgtc gtacgtcaac agagcacaaa gccaagtcag ccatttttt     7620 cacttaatac atacacactt tattgcattt ttgtttttg tttttgtttt gaatcagtaa     7680
tacaaagcat gcaaggctgc catgtcccaa gcctgtgtgg ggctggagag ctggagcgga    7740
cacagcagta tgcctgccct tcactgcctg tagcttatgg cccagtaggg gagacaaaca    7800
taaatcaaaa cacatgtgtt tatggtagat gtggataagt gctacagagg agaaacaggg    7860
ttgtgaaaga agaatggagc aggaagttgc ggtcccaatt cagactatgg tgaaggggag    7920
agcttctgag ttgactttga ggaggaataa gagttaggtg ttgctgggaa gggaaagag     7980 gggatgcgta gggacttttt ttctgcagga aggctctgag gcagaaaact ccatttgagg    8040
aactttaaag aaaccagcag gtgggaagca atgggaggta gctggggtat acggaataaa    8100
ttagagcatc aaagcacact gaggattaag gggtgaggga gaggaagcta tcaagggtga    8160
gtgttagctt tacagcttga agaacatggt gaatggaggt gtcttcattc attgatttag    8220
```

-continued

```
ggaagtctca gggaaaaatg tttggagtac tccttagata aattcatctt ttagtgctag    8280
acatgttagg attctgtgag aagaaaatgt ctaaggattt acactagttg ggacttactc    8340
agtgacagaa gatccaatgc aaattattta agcagaaaag gaatttcttg cctcacctga    8400
ctaaaaagtt gagcaagata agcttcaggt acaacctgac ccagactgca aatgatgttg    8460
ctaggacctg gttccaccca tttcttggct ctgcttcttt tgcactgact ccagtctcta    8520
agctctctcc cctgtgggag ccacattgct gcagcctctc ttcacctcca cctagggtga    8580
ggtctgctgg gaaaatagga gagttatttc cagtacctct cccaaaagtc ctaatgtaca    8640
ctccgacttg gaggacctta tggtgaccgc gtcatggggg accacaagat gcacccaacc    8700
ctaaaccaat cactgcgccc aggggaatgt gaaggtgtga ttggctcagg ctgggctgtg    8760
tgctctgccc agaccaatgg acacagtgtg ggggaggcat aggtccccag agggaaatct    8820
gcagctgttg ggaacaagga gagaagatgt tagcatgtgt ggggaagaat atttatcctc    8880
tgtgtgatca ttcttagcaa agagtagttc aaattatttg tggagctgct tggaggctgg    8940
ggtgaaatgg gttcagccag tgtctggaaa cctcacaaag tcattttcta agtaagcact    9000
cagggtgaag agagcttgta gcatctttag tgtggtccat gaaagaatat gtataaaggc    9060
aaactcctcc gaaaaccttg tccaaaagct agtattgtac taaagaatag taaggattgg    9120
gtttataaaa tatcttaggc caattcacct gtagtccaca ccataatttc agaggaaaat    9180
tttcaggcag tggtcaacta catttagata aacgttttcc caagtggtta tactagaatt    9240
tttgcttcag ttgcccagtg tttattggga ttcagagatg agacactctc caggaaacta    9300
gcagggaaga tgtgaaagca aatacaccac cacatgaaga atcttgctat aatggacatg    9360
catacaaaac aaagcagcaa tgcagacttc attctgctgt cacagaagcc ttacagaggt    9420
gacagttaat gccttagtga gttttgaagg atgaatagga gtacaccaaa agggaaagag    9480
atggcggatg tttcacacaa gaggaagggt gtgagcaacg ttttagtgac ctgacatagc    9540
attgtatgct tttggaggca gtgcagattc aggcttgtat tccagcagtc cctctaatca    9600
tgttgtatag ctctccaaac ttgttttatcc atttataaag tacaattcct ctctcatgga    9660
ttgttaggag aattaaacag aaatgcaaag tactcagctc tgctacagta agagctgaac    9720
aaacctttgc cattgccatt atagtctggc aggagtgctg tgggtgatga ttgaggaggg    9780
gagagattag gagtcagatc atgaaatgct ttgattgcta tagtagggag catggctctt    9840
atcctaaagg cattagagag ccttgtaaat ggctctgaaa tgaaggatca gatttgtgtc    9900
accgtgggaa ggaataaaaa gtccacctgg gggactactg gcagaaaccc agtgaaggaa    9960
cgataaagac atgaagttgt aagtccctga tggttctggt ggtgggggt ggctatgtga    10020 cagacagaag agatatttag gagtagtcct agagcatcgc tgggtacaaa ctcagccagt    10080
tgctgtgact gaccaaacag gcccctggct tgtaacccct aggaccaggc ctgatacttt    10140
atagattttg tcctgcttaa ttctcccaat aacaaaaaca ttttcccagg tgcccagctc    10200
caaagcctat gtccttcctc actgtgaagg agagtgacaa agctggatgg gtccttccgt    10260
ctcccatcct actccatgcc tagcagggtg cccagcactg aatggcagct aatatctatt    10320
tgagaaaaca atgaaagcaa gtgcctcata ccattcccca tgtctgggt aacttctccc    10380 accccactgc ctgtgcaagc cctccccacc tctcagaacc cagtccccag cccatctcac    10440
catgtcagct tgctccacat cctcagccca caaagctttc cctggcgccg agggggcaga    10500
gagagcctcc tgggcatcct gaacgattcc ttcgaccctc agccctgctg ctggtggcct    10560
```

```
ctgtgccagc tctacggtca gaggtcaggg tgtggcttcc taagacatta ctgctttatg   10620
gacagtctgg ctttgagtta gtgtggctct tgttgagatc ccaaaatata gtttggcttt   10680 tccctgcat cagttttctt tccaggaaac agaaaatgga gtttctcgga gtctggggtt   10740 aagggactg aagtgatgct gccccattct caccaaccac ccacaaggt cctggcccca   10800 agcgggtgaa ttccttgcct gcctggacca ttctcaaagt cagggcagct ttggcttcct   10860
ctccattttc aagttttcat accttatcag ggcagtctga ctttgaagca tcattttccc   10920
tggagtcctc agggctctca atgaagcatg aatcccctg tcctggggtg aggatgcaga   10980
tgagggcctg gtgggtgtgt ggtgtggccc ttctcccatt tatgtcatga actttggcag   11040
acttgtacta tttgggtgct ctgtccccat ctccacccct gtgggtcaat gcaaacagaa   11100
caactcctca catttgtgag ggccccacga ggtgcttgtc tatgccttag attatttgag   11160
tgacagtggc cttatgactg aggtaggggc agtattacta tttttaaata atattttctc   11220
ctgcatgttt ttgtttaaat gtgggaactc taggaagtac atagaagaaa aaaaaaggg   11280 ctgtttccc atcatgtttg ctcttctgta ctccccagt gtctaccctg ctgttaatca   11340
tctttgttat tctccaggac agatattttt tgagatggag tctcactctg ttgcccaggc   11400
tggaatgcag tggcgcgatc ttgggtcact gcaacctccc actcctgagt tcaagtgatt   11460
gtcatgcctc agcctcctga gtagctgcga ttataggcac gcgccaccac gctcacctaa   11520 ttttgtatt tttagtagag acaaggtgtc accatgttgg ccaggctggt ctcaaactcc   11580
tgacctcagg tgattggcct ggcttggcat cccaaagtac tgggattaca ggcctgagcc   11640
actatgccca aactttagga aagatagtat tatctccatt ttatagacaa taaaagttta   11700
agctcaaagt catataacta ataagcggca cagttataag gagaatgtgc acagttcttc   11760
tcatcaccag tctaatgcaa tagtaggact tcaatgcaca attgttgaat tcagaaagat   11820
aaataagact atttgtttat ttatttattt atttatttat tttgagacag cgtgtcattc   11880
tgtttcccag gctggagtgc agtggtgtga cctcggctta ctgaaacctc agcctcctgg   11940
gttcaagtgg ttcccatacc tcagcctccc gagtagctgg gattacaggc atgtgccacc   12000
aagcccagct gatttttata tttttagtag agatggggtt tcaccatgtt ggccaggcta   12060
agattattta taatagtctt ataaatgtgt gtttgtataa gggaccacct ggagggtgtg   12120
gcggacctgc ctgaaatgtt agatcaggga tctgatggaa agggaacttg gacggaattc   12180
ggaagaagcc atcttttatg aagaataaca gagccttttt cccctctctg ccctcaaaca   12240
gatactgaca agttaaaaaa cataatgcag gtggcagagc ccagagtcag agatgtcatc   12300
aacagcatgg agcatgctat tgtttcccgg agccctcgca tccgctacaa ccctggcctg   12360
gatgccaaac tcctctacat ccctctggct aagttgccca ccctgtgac agatttcatc   12420 ctaagccggt accttccaag gccagcggac agtgtctaaa ctggggagga tcaatgggtc   12480
agtggagcct agaagtgggg gaggaaggaa ggaccgtggg gtcacaaaag gtggtatcgg   12540
ttatcctggg ggcattggct gcaaaggaag cttggctcag ctgacaccca ctgctgtcga   12600
atttaccagt aacttctaac agaaggtgaa tgcctcttcc caccctctgg accccacag   12660 aaacctgagg tggtctttgc aggttcagcg atctgcagca atagctccaa ggacgtctgt   12720
cacccaatca ggatacagct ttttctggtc ctggaaaagt catggagaag aaaaccagct   12780
cctgtggaat catgagcccc tttcagttat cactgccact gagaaatact gtgggataat   12840
cttgcctcca ggagaatcta accaccttcc taatgggtcc ctcaatatgc ataacttcat   12900
tcacataacc cattactgaa gtatgcggta gggcagatag ggagtgcaag attaaatcag   12960
```

-continued

```
acaaaagttt aaaatatttt ctttctttttt agattcttct atctataggt tattgggatc    13020
cacatgaaat aacattcatt tatttaatca ccattaattt ttcaaatatt tattgagtgc    13080
ctactaccta ccgggcactt tgtaggtgct ggggggaatat aaagatgatt aaatcatggt   13140
cttggttttt tattgtttat tttgtgtttt gctttgcttt gttttagcac aatatctagt    13200
agctgagtta ggacaaacag cgatagaagg aatagaaatc agaatacaaa ttttttagagc  13260 tatgaaggac cctggaggtc ttcatccaat acttcacaag cttggctgta ccttgtatca   13320
cccagtcaat taaaaaatac agactcctgt gccaatatta gaaatctga ttcagtagga    13380 ctgagataag gtccagaaat atgtgtttat aacaaggacc tatatgattc tgatgcaccc   13440
gagcaacttg gagccaccaa taattccata gaataagtaa cttaacactc agaggggaa    13500 gtgacctacc caagccccca gtttagtaac taagacaagg atagaaatga ggcattcaga   13560
ctcccagacc aggattattt ttcagttata ggaaaatcaa tttctcaaat tagtaacact   13620
gtcaaataag tcattgaact aatttttttt aaaaaaagac ttaaactcct gggtcatatg   13680
aagttctgtg gaagagactt tttttttttat cttgataaat ggtcatgtaa taaaggtcaa   13740
atgtgatttt tttaactaaa atatctttaa tttgggtctc ttcaacatct gaaaataata   13800
aaatataatc caggtacatc tgcaaagact ccaaataagg taacactcac gggttccagg   13860
ggttagctta tagatatatc tttagggagc tactgtgcaa ctcactacag tttgttgttt   13920
gcagcacttc tattcctggc accaaattct aaatcagata gaatgcattc aacaagtaac   13980
agaaaaacca actcacactg gcttagacaa tgaagagtga gggcagggcc cagtggctga   14040
atgatggcat tgaggctgta ggctcttttct acttctttgc tccgctgccc acagttttat   14100 ctttacccctt tgttgctgtg gtgtgactgc caggcaaagg gaactctaca tttcctcatt   14160
cacaacttag agaagaagaa agagcctgcc tttccacagc attcaacatt gaagaagttt   14220
ctttcttaga gccctcatca tgtgtctcct tgaatctcat tggcccaaat tggtttaggc   14280
ttgtccaccc ctggcaaaga ggtaaattgc catgaattgc ttagattaat cacgggacag   14340
atgggatgtt gggaaatcag tcacaatgtc tactaccttg gaaaatgcaa aactcagaca   14400
ttatgctgtt gagagggttg aacaaaggtc aaaaataaat tttctgaaga cacaaaaatt   14460
tactaagggg aaactggcta ggtaa                                          14485
```

<210> SEQ ID NO 4
<211> LENGTH: 313
<212> TYPE: PRT
<213> ORGANISM: Homo sapiens

<400> SEQUENCE: 4

```
Leu Ala Val Phe Val Gly Leu Tyr Tyr Leu Leu His Trp Tyr Arg Glu
 1               5                  10                  15

Arg Gln Val Leu Ser His Leu Arg Asp Lys Tyr Val Phe Ile Thr Gly
            20                  25                  30

Cys Asp Ser Gly Phe Gly Lys Leu Leu Ala Arg Gln Leu Asp Ala Arg
        35                  40                  45

Gly Leu Arg Val Leu Ala Ala Cys Leu Thr Glu Lys Gly Ala Glu Gln
    50                  55                  60

Leu Arg Gly Gln Thr Ser Asp Arg Leu Glu Thr Val Thr Leu Asp Val
65                  70                  75                  80

Thr Lys Thr Glu Ser Val Ala Ala Ala Ala Gln Trp Val Lys Glu Cys
                85                  90                  95
```

-continued

```
Val Arg Asp Lys Gly Leu Trp Gly Leu Val Asn Asn Ala Gly Ile Ser
        100                 105                 110

Leu Pro Thr Ala Pro Asn Glu Leu Leu Thr Lys Gln Asp Phe Val Thr
        115                 120                 125

Ile Leu Asp Val Asn Leu Leu Gly Val Ile Asp Val Thr Leu Ser Leu
        130                 135                 140

Leu Pro Leu Val Arg Arg Ala Arg Gly Arg Val Val Asn Val Ser Ser
145                 150                 155                 160

Val Met Gly Arg Val Ser Leu Phe Gly Gly Gly Tyr Cys Ile Ser Lys
            165                 170                 175

Tyr Gly Val Glu Ala Phe Ser Asp Ser Leu Arg Arg Glu Leu Ser Tyr
            180                 185                 190

Phe Gly Val Lys Val Ala Met Ile Glu Pro Gly Tyr Phe Lys Thr Ala
            195                 200                 205

Val Thr Ser Lys Glu Arg Phe Leu Lys Ser Phe Leu Glu Ile Trp Asp
        210                 215                 220

Arg Ser Ser Pro Glu Val Lys Glu Ala Tyr Gly Glu Lys Phe Val Ala
225                 230                 235                 240

Asp Tyr Lys Lys Ser Ala Glu Gln Met Glu Gln Lys Cys Thr Gln Asp
                245                 250                 255

Leu Ser Leu Val Thr Asn Cys Met Glu His Ala Leu Ile Ala Cys His
            260                 265                 270

Pro Arg Thr Arg Tyr Ser Ala Gly Trp Asp Ala Lys Leu Leu Tyr Leu
        275                 280                 285

Pro Met Ser Tyr Met Pro Thr Phe Leu Val Asp Ala Ile Met Tyr Trp
    290                 295                 300

Val Ser Pro Ser Pro Ala Lys Ala Leu
305                 310
```

ISOLATED HUMAN DEHYDROGENASEPROTEINS, NUCLEIC ACID MOLECULES ENCODING THESE HUMAN DEHYDROGENASE PROTEINS, AND USES THEREOF

RELATED APPLICATIONS

The present application is a divisional of U.S. application Ser. No. 09/876,216, filed on Jun. 8, 2001, and issued on Apr. 8, 2003 as U.S. Pat. No. 6,544,764, which claims priority of U.S. provisional application 60/247,922 filed on Nov. 14, 2000.

FIELD OF THE INVENTION

The present invention is in the field of dehydrogenases that are related to the retinol dehydrogenase subfamily, recombinant DNA molecules and protein production. The present invention specifically provides novel dehydrogenase polypeptides and proteins and nucleic acid molecules encoding such peptide and protein molecules, all of which are useful in the development of human therapeutics and diagnostic compositions and methods.

BACKGROUND OF THE INVENTION

Dehydrogenases, particularly members of the retinol dehydrogenase subfamily, are a major target for drug action and development. Accordingly, it is valuable to the field of pharmaceutical development to identify and characterize previously unknown members of these subfamily of dehydrogenases. The present invention advances the state of the art by providing a previously unidentified human dehydrogenases that have homology to members of the retinol dehydrogenase subfamilies.

Retinol Dehydrogenase

The human protein, and encoding gene, provided by the present invention is related to the dehydrogenase protein family, and shows a particularly high degree of similarity to retinol dehydrogenases. Retinol dehydrogenase catalyzes the primary and rate-limiting step in the synthesis of retinoic acid from retinol. Retinoic acid controls a wide variety of important biological systems by regulating eukaryotic gene expression (Chai et al., *J Biol Chem* 1995 Feb. 24;270(8):3900–4). Retinoic acid is a powerful regulator of gene expression; novel retinol dehydrogenases are useful for modulating the synthesis of retinoic acid and, therefore, are useful for modulating gene expression in numerous important biological systems. Furthermore, retinol dehydrogenase 4 is useful for catalyzing the synthesis of not only retinoic acid, but also dihydrotestosterone from 3alpha-androstanediol (Gough et al., *J Biol Chem* 1998 Jul. 31;273(31):19778–85). Like retinoic acid, dihydrotestosterone is also a powerful modulator of gene expression. Retinol dehydrogenase 4 also oxidizes all-trans-retinol and 13-cis-retinol to corresponding aldehydes and oxidizes the 3alpha-hydroxysteroids androstane-diol and androsterone to dihydrotestosterone and androstanedione, respectively (Gough et al., *J Biol Chem* 1998 Jul. 31;273(31):19778–85).

Retinoic acid is the active form of vitamin A, which is necessary for the normal growth and differentiation of the epidermis. Retinaldehyde is an intermediate in the synthesis of retinoic acid from retinol in epidermal keratinocytes. Retinol dehydrogenase catalyzes the initial and rate-limiting step that generates retinaldehyde from retinol (Jurukovski et al., *Mol Genet Metab* 1999 May;67(1):62–73). Therefore, novel retinol dehydrogenases are useful for modulating the growth and differentiation of the epidermis, such as for treating epidermal/skin disorders or enhancing skin health and appearance.

Vitamin A is a pigment essential to vision. Vitamin A comes from the enzymatic conversion of carotenoids, yellow pigments common to carrots and other vegetables, to retinol. Deficiency of vitamin A and insufficient retinol production leads to a variety of maladies in humans and experimental animals. Symptoms of deficiency include vision related disorders such as xerophthalmia and night blindness; dry skin and dry mucous membranes; retarded development and growth; and sterility in male animals.

Cleavage of beta-carotene yields two molecules of retinol; oxidation of retinol forms retinal. Retinal and opsin combine to produce rhodopsin, a visual pigment found in nature. The excitation of rhodopsin with visible light triggers a series of photochemical reactions and conformational changes in the molecule which result in the electrical signal to the brain that are the basis of visual transduction (Lehninger et al. (1993) *Principles of Biochemistry*, Worth Publishers, New York, N.Y.).

Retinol dehydrogenase (RoDH) catalyzes the conversion of retinol to retinal; retinal dehydrogenase converts retinal to retinoate. Retinoate is a retinoid and a hormone that controls numerous biological processes by regulating eukaryotic gene expression. Retinoids, like steroid and thyroid hormones, diffuse directly across the plasma membrane and bind to intracellular receptor proteins. Binding activates the receptors that interact with signaling pathways (Vettermann et al. (1997) *Mol. Carcinog.* 20: 58–67), and regulate the transcription of specific genes, particularly those mediating vertebrate development (Alberts et al. (1994) *Molecular Biology of the Cell*, Garland Publishing, Inc., New York, N.Y.). Retinol is known to be important in epithelial development (Haselbeck et al. (1997) *Dev. Dyn.* 208: 447–453; and Attar et al. (1997) *Mol. Endocrinol.* 11: 792–800) and in the development of the central nervous system (Maden et al. (1997) *Development* 124: 2799–2805). In Maden's studies on quail embryos, absence of vitamin A, lead to severe deficits including lack of a posterior hindbrain. Conversely, injection of retinol before gastrulation of the embryo prevented positional apoptosis and corrected the CNS defects.

The universal chromophore of visual pigments is 11-cis retinaldehyde, which is generated by 11-cis retinol dehydrogenase, a membrane-bound enzyme abundantly expressed in the retinal pigment epithelium of the eye. The gene that encodes 11-cis retinol dehydrogenase may be involved in hereditary eye diseases (Simon et al. (1996) *Genomics* 36: 424–430).

Chai et al. have identified, cloned, and expressed two isoforms of retinol dehydrogenase, RoDH(I) and (RoDH(II) (1995, *J. Biol. Chem.* 270: 28408–28412). The deduced amino acid sequence shows that RoDH(I) and RoDH(II) are short-chain dehydrogenases/reductases that share 82% identity. Retinol is the substrate for RoDH(II) which has a higher affinity for NADP than NAD and is stimulated by ethanol and phosphatidyl choline. Although RoDH(II) is not inhibited by the medium-chain alcohol dehydrogenase inhibitor, 4-methylpyrazole, it is inhibited by phenylarsine oxide and carbenoxolone. Chai et al. reported detection of RoDH(I) and RoDH(II) mRNA in rat liver, but RNase protection assays revealed RoDH(I) and RoHD(II) mRNA in kidney, lung, testis, and brain. Based on these data, Chai et al. concluded that RoDH has tissue specific expression.

The retinol signaling pathway plays an important role in human disorders and diseases. Retinoic acid receptors (RARs; -alpha, -beta, and -gamma) are retinoid-activated transcription factors, which mediate effects of retinoids on gene expression. Alterations in receptor expression or function could interfere with the retinoid signaling pathway. Interference with the pathway may enhance cancer development. Vitamin A analogs (retinoids) which interact with RARs, suppress oral and lung carcinogenesis in animal models and prevent the development of tumors in head, neck, and lung cancer patients (*Lotan R.* 1997 *Environ. Heath Perspect.* 105 Suppl. 4: 985–988). Lotan reported that RAR beta expression is lost at early stages of carcinogenesis in the aerodigestive tract.

Retinol dehydrogenase is implicated in embryonic development. The studies of Maden et al. (supra) suggest that retinol may play a significant role in controlling apoptosis during development of the central nervous system. Retinoids are also implicated in epidermal development. Attar et al. (1997, *Mol. Endocrinol.* 11: 792–800) showed that disruption of epidermal barrier function results in extremely high incidences of neonatal mortality in pups.

Retinoic acid acts as an important signal during development, particularly in the development of the neural axis, and defects in retinoic acid synthesis due to defects in retinaldehyde dehydrogenase proteins or the encoding genes can severely affect development and lead to early embryonic death. For example, targeted disruption of the retinaldehyde dehydrogenase 2 gene in the mouse has been shown to cause embryonic death at midgestatation. Furthermore, such mutated embryos lack axial rotation, exhibit shortening along the anterioposterior axis and have an open neural tube, and lack limb buds. Additional severe defects were observed in the hearts, frontonasal regions, and otocysts of these mutated embryos. These defects were caused by a blockage of embryonic retinoic acid synthesis. These experiments established that retinoic acid synthesized by the postimplantation embryo is a critical developmental hormone and that a lack of retinoic acid causes early embryonic death (Niederreither et al., *Nature Genet.* 21: 444–448, 1999).

In addition, retinol dehydrogenase activity is linked to hereditary eye diseases (Simon et al. (1996) *Genomics* 36: 424–430). Autosomal recessive childhood-onset severe retinal dystrophy (arCSRD) is a heterogeneous group of disorders that affect rod and cone photoreceptors simultaneously. Disease genes implicated in arCSRD are expected to encode proteins present in the neuroretina or in the retinal pigment epithelium (RPE). RPE65, a tissue-specific and evolutionarily highly conserved 61 kD protein, is the first disease gene in this group of inherited disorders that is expressed exclusively in RPE, and may play a role in vitamin A metabolism of the retina (Gu et al. (1997) *Nat. Genet.* 17: 194–197).

Pityriasis rubra pilaris (PRP) is an idiopathic erythematous scaling eruption which can be difficult to distinguish from psoriasis. The expression of RoDH(II) in the retinol signaling pathway may be of pathogenetic importance in the diagnosis of PRP (Magro, C. M. and Crowson, A. N. (1997) *J Cutan. Pathol.* 24: 416–424).

For a further review of dehydrogenases, particularly retinol dehydrogenases, see Chai et al, *Gene* 1996 Mar. 9;169 (2):219–22; Chai et al., *J Biol Chem* 1997 Dec. 26;272(52): 33125–31; Gough et al., *J Biol Chem* 1998 Jul. 31;273(31): 19778–85; Ono et al., *Molec. Cell. Biol.* 18: 6939–6950, 1998; Wang et al., *J Biol. Chem.* 271: 16288–16293, 1996; and Zhao et al., *Europ. J. Biochem.* 240: 15–22, 1996.

The discovery of new human dehydrogenase proteins, particularly members of the retinol dehydrogenase subfamily, and the polynucleotides encoding these proteins satisfies a need in the art by providing new compositions which are useful in the diagnosis, prevention and treatment of biological processes associated with human diseases.

SUMMARY OF THE INVENTION

The present invention is based in part on the identification of amino acid sequences of human dehydrogenase polypeptides and proteins that are related to the retinol dehydrogenase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate dehydrogenase activity in cells and tissues that express the dehydrogenase. The protein of the present invention is expressed in human placenta, as indicated by the library source of the cDNA clone (indicated in FIG. 1).

DESCRIPTION OF THE FIGURE SHEETS

FIG. 1 provides the nucleotide sequence of a cDNA molecule that encodes the dehydrogenase of the present invention. (SEQ ID NO:1) In addition, structure and functional information is provided, such as ATG start, stop and tissue distribution, where available, that allows one to readily determine specific uses of inventions based on this molecular sequence. The protein of the present invention is expressed in human placenta, as indicated by the library source of the cDNA clone (indicated in FIG. 1).

FIG. 2 provides the predicted amino acid sequence of the dehydrogenase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the dehydrogenase of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 17 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a dehydrogenase or part of a dehydrogenase and are related to the retinol dehydrogenase subfamily. Utilizing these sequences, additional genomic sequences were assembled and transcript and/or cDNA sequences were isolated and characterized. Based on this analysis, the present invention provides amino acid sequences of human dehydrogenase polypeptides that are related to the retinol dehydrogenase subfamily, nucleic acid sequences in the form of transcript sequences, cDNA sequences and/or genomic sequences that encode these dehydrogenase polypeptide, nucleic acid variation (allelic information), tissue distribution of expression, and information about the closest art known protein/peptide/domain that has structural or sequence homology to the dehydrogenase of the present invention.

In addition to being previously unknown, the peptides that are provided in the present invention are selected based on their ability to be used for the development of commercially important products and services. Specifically, the present peptides are selected based on homology and/or structural relatedness to known dehydrogenases of the retinol dehydrogenase subfamily and the expression pattern observed. The protein of the present invention is expressed in human placenta, as indicated by the library source of the cDNA clone (indicated in FIG. 1). The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known retinol dehydrogenase family or subfamily of dehydrogenases.

Specific Embodiments

Peptide Molecules

The present invention provides nucleic acid sequences that encode protein molecules that have been identified as being members of the dehydrogenase family and are related to the retinol dehydrogenase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the dehydrogenases or peptides of the present invention, dehydrogenases or peptides, or peptides/proteins of the present invention.

The present invention provides isolated peptide and protein molecules that consist of, consist essentially of, or comprise the amino acid sequences of the dehydrogenase polypeptide disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30%, (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the dehydrogenase polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated dehydrogenase polypeptide can be purified from cells that naturally express it, purified from cells that have been altered to express it (recombinant), or synthesized using known protein synthesis methods. The protein of the present invention is expressed in human placenta, as indicated by the library source of the cDNA clone (indicated in FIG. 1). For example, a nucleic acid molecule encoding the dehydrogenase polypeptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have, additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the dehydrogenase polypeptide of the present invention are the naturally occurring mature proteins. A brief description of how various types of these proteins can be made/isolated is provided below.

The dehydrogenase polypeptides of the present invention can be attached to heterologous sequences to form chimeric or fusion proteins. Such chimeric and fusion proteins comprise a dehydrogenase polypeptide operatively linked to a heterologous protein having an amino acid sequence not substantially homologous to the dehydrogenase polypeptide. "Operatively linked" indicates that the dehydrogenase polypeptide and the heterologous protein are fused in-frame.

The heterologous protein can be fused to the N-terminus or C-terminus of the dehydrogenase polypeptide.

In some uses, the fusion protein does not affect the activity of the dehydrogenase polypeptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant dehydrogenase polypeptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A dehydrogenase polypeptide-encoding nucleic acid can be cloned into such an expression vector such that the fusion moiety is linked in-frame to the dehydrogenase polypeptide.

As mentioned above, the present invention also provides and enables obvious variants of the amino acid sequence of the peptides of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the dehydrogenase polypeptides of the present invention. The degree of homology/identity present will be based primarily on whether the peptide is a functional variant or non-functional variant, the amount of divergence present in the paralog family, and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, word length=12 to obtain nucleotide sequences homologous to the nucleic acid molecules of the invention. BLAST protein searches can be performed with the XBLAST program, score=50, word length=3, to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used. See http://www.ncbi.nlm.nih.gov.

Full-length pre-processed forms, as well as mature processed forms, of proteins that comprise one of the peptides of the present invention can readily be identified as having complete sequence identity to one of the dehydrogenase polypeptides of the present invention as well as being encoded by the same genetic locus as the dehydrogenase polypeptide provided herein. The gene encoding the novel dehydrogenase protein of the present invention is located on a genome component that has been mapped to human chromosome 12 (as indicated in FIG. 3), which is supported by multiple lines of evidence, such as STS and BAC map data.

Allelic variants of a dehydrogenase polypeptide can readily be identified as being a human protein having a high degree (significant) of sequence homology/identity to at least a portion of the dehydrogenase polypeptide as well as being encoded by the same genetic locus as the dehydrogenase polypeptide provided herein. Genetic locus can readily be determined based on the genomic information provided in FIG. 3, such as the genomic sequence mapped to the reference human. The gene encoding the novel dehydrogenase protein of the present invention is located on a genome component that has been mapped to human chromosome 12 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a dehydrogenase polypeptide encoding nucleic acid molecule under stringent conditions as more fully described below.

FIG. 3 provides information on SNPs that have been found in a gene encoding the dehydrogenase of the present invention. SNPs were identified at 17 different nucleotide positions. Some of these SNPs, which are located outside the ORF and in introns, may affect control/regulatory elements.

Paralogs of a dehydrogenase polypeptide can readily be identified as having some degree of significant sequence homology/identity to at least a portion of the dehydrogenase polypeptide, as being encoded by a gene from humans, and as having similar activity or function. Two proteins will typically be considered paralogs when the amino acid sequences are typically at least about 40–50%, 50–60%, and more typically at least about 60–70% or more homologous through a given region or domain. Such paralogs will be encoded by a nucleic acid sequence that will hybridize to a dehydrogenase polypeptide encoding nucleic acid molecule under moderate to stringent conditions as more fully described below.

Orthologs of a dehydrogenase polypeptide can readily be identified as having some degree of significant sequence homology/identity to at least a portion of the dehydrogenase polypeptide as well as being encoded by a gene from another organism. Preferred orthologs will be isolated from mammals, preferably primates, for the development of human therapeutic targets and agents. Such orthologs will be encoded by a nucleic acid sequence that will hybridize to a dehydrogenase polypeptide encoding nucleic acid molecule under moderate to stringent conditions, as more fully described below, depending on the degree of relatedness of the two organisms yielding the proteins.

Non-naturally occurring variants of the dehydrogenase polypeptides of the present invention can readily be generated using recombinant techniques. Such variants include, but are not limited to deletions, additions and substitutions in the amino acid sequence of the dehydrogenase polypeptide. For example, one class of substitutions is conserved amino acid substitutions. Such substitutions are those that substitute a given amino acid in a dehydrogenase polypeptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent are found in Bowie et al., Science 247:1306–1310 (1990).

Variant dehydrogenase polypeptides can be fully functional or can lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallography, nuclear magnetic resonance, or photoaffinity labeling (Smith et al., J. Mol. Biol. 224:899–904 (1992); de Vos et al. Science 255:306–312 (1992)).

The present invention further provides fragments of the dehydrogenase polypeptides, in addition to proteins and peptides that comprise and consist of such fragments. Particularly those comprising the residues identified in FIG. 2. The fragments to which the invention pertains, however, are not to be construed as encompassing fragments that have been disclosed publicly prior to the present invention.

As used herein, a fragment comprises at least 8, 10, 12, 14, 16 or more contiguous amino acid residues from a dehydrogenase polypeptide. Such fragments can be chosen based on the ability to retain one or more of the biological activities of the dehydrogenase polypeptide, or can be chosen for the ability to perform a function, e.g., act as an immunogen. Particularly important fragments are biologically active fragments, peptides that are, for example about 8 or more amino acids in length. Such fragments will typically comprise a domain or motif of the dehydrogenase polypeptide, e.g., active site. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE, HMMer, eMOTIF, etc.). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in dehydrogenase polypeptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the dehydrogenase polypeptides of the present invention also encompass derivatives or analogs in which a substituted amino acid residue is not one encoded by the genetic code, in which a substituent group is included, in which the mature dehydrogenase polypeptide is fused with another compound, such as a compound to increase the half-life of the dehydrogenase polypeptide (for example, polyethylene glycol), or in which the additional amino acids are fused to the mature dehydrogenase polypeptide, such as a leader or secretory sequence or a sequence for purification of the mature dehydrogenase polypeptide, or a pro-protein sequence.

Protein/Peptide Uses

The proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its ligand or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as research products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, dehydrogenases isolated from humans and their human/mammalian orthologs serve as targets for identifying agents for use in mammalian therapeutic applications, e.g. a human drug, particularly in modulating a biological or pathological response in a cell or tissue that expresses the dehydrogenase. The dehydrogenase proteins of the present invention are expressed in human placenta, as indicated by the library source of the cDNA clone (indicated in FIG. 1). A large percentage of pharmaceutical agents are being developed that modulate the activity of dehydrogenases, particularly members of the retinol dehydrogenase subfamily (see Background of the Invention). The structural and functional information provided in the Background and Figures provide specific and substantial uses for the molecules of the present invention, particularly in combination with the expression information provided in FIG. 1. The protein of the present invention is expressed in human placenta, as indicated by the library source of the cDNA clone (indicated in FIG. 1). Such uses can readily be determined using the information provided herein, that which is known in the art, and routine experimentation.

The proteins of the present invention (including variants and fragments that may have been disclosed prior to the present invention) are useful for biological assays related to dehydrogenases that are related to members of the retinol dehydrogenase subfamily. Such assays involve any of the known dehydrogenase functions or activities or properties useful for diagnosis and treatment of dehydrogenase-related conditions that are specific for the subfamily of dehydrogenases that the one of the present invention belongs to, particularly in cells and tissues that express the dehydrogenase. The dehydrogenase proteins of the present invention are expressed in human placenta, as indicated by the library source of the cDNA clone (indicated in FIG. 1).

The proteins of the present invention are also useful in drug screening assays, in cell-based or cell-free systems. Cell-based systems can be native, i.e., cells that normally express the dehydrogenase, as a biopsy or expanded in cell culture. The protein of the present invention is expressed in human placenta, as indicated by the library source of the cDNA clone (indicated in FIG. 1). In an alternate embodiment, cell-based assays involve recombinant host cells expressing the dehydrogenase.

The polypeptides can be used to identify compounds that modulate dehydrogenase activity. Both the dehydrogenase of the present invention and appropriate variants and fragments can be used in high-throughput screens to assay candidate compounds for the ability to bind to the dehydrogenase. These compounds can be further screened against a functional dehydrogenase to determine the effect of the compound on the dehydrogenase activity. Further, these compounds can be tested in animal or invertebrate systems to determine activity/effectiveness. Compounds can be identified that activate (agonist) or inactivate (antagonist) the dehydrogenase to a desired degree.

Therefore, in one embodiment, retinol dehydrogenase or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising retinol dehydrogenase may be administered to a subject to prevent or treat a disorder associated with increased apoptosis including, but not limited to, those listed above.

In still another embodiment, an agonist which is specific for retinol dehydrogenase may be administered to prevent or treat a disorder associated with increased apoptosis including, but not limited to, those listed above.

In a further embodiment, a vector capable of expressing retinol dehydrogenase, or a fragment or a derivative thereof, may be used to prevent or treat a disorder associated with increased apoptosis including, but not limited to, those listed above.

In cancer, where retinol dehydrogenase promotes cell proliferation, it is desirable to decrease its activity. Therefore, in one embodiment, an antagonist of retinol dehydrogenase may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for retinol dehydrogenase may be used directly as an antagonist, or indirectly as a targeting or delivery mechanism for bringing a pharmaceutical agent to cells or tissue which express retinol dehydrogenase.

In another embodiment, a vector expressing the complement of the polynucleotide encoding retinol dehydrogenase may be administered to a subject to prevent or treat a cancer including, but not limited to, the types of cancer listed above.

In inflammation, where retinol dehydrogenase promotes cell proliferation, it is desirable to decrease its activity. Therefore, in one embodiment, an antagonist of retinol dehydrogenase may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for retinol dehydrogenase may be used directly as an antagonist, or indirectly as a targeting or delivery mechanism for bringing a pharmaceutical agent to cells or tissue which express retinol dehydrogenase.

Further, the dehydrogenase polypeptides can be used to screen a compound for the ability to stimulate or inhibit interaction between the dehydrogenase and a molecule that normally interacts with the dehydrogenase, e.g. a ligand or a component of the signal pathway that the dehydrogenase normally interacts. Such assays typically include the steps of combining the dehydrogenase with a candidate compound under conditions that allow the dehydrogenase, or fragment, to interact with the target molecule, and to detect the formation of a complex between the protein and the target or to detect the biochemical consequence of the interaction with the dehydrogenase and the target, such as any of the associated effects of signal transduction.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries). (Hodgson, Bio/technology, 1992, Sep. 10(9);973–80).

One candidate compound is a soluble fragment of the dehydrogenase that competes for ligand binding. Other candidate compounds include mutant dehydrogenases or appropriate fragments containing mutations that affect dehydrogenase function and thus compete for ligand. Accordingly, a fragment that competes for ligand, for example with a higher affinity, or a fragment that binds ligand but does not allow release, is within the scope of the invention.

The invention further includes other end point assays to identify compounds that modulate (stimulate or inhibit) dehydrogenase activity. The assays typically involve an assay of events in the dehydrogenase mediated signal transduction pathway that indicate dehydrogenase activity. Thus, the phosphorylation of a protein/ligand target, the expression of genes that are up- or down-regulated in response to the dehydrogenase dependent signal cascade can be assayed. In one embodiment, the regulatory region of such genes can be operably linked to a marker that is easily detectable, such as luciferase. Alternatively, phosphorylation of the dehydrogenase, or a dehydrogenase target, could also be measured.

Any of the biological or biochemical functions mediated by the dehydrogenase can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric dehydrogenases in which any of the protein's domains, or parts thereof, can be replaced by heterologous domains or subregions. Accordingly, a different set of signal transduction components is available as an end-point assay for activation. This allows for assays to be performed in other than the specific host cell from which the dehydrogenase is derived.

The dehydrogenase polypeptide of the present invention is also useful in competition binding assays in methods designed to discover compounds that interact with the dehydrogenase. Thus, a compound is exposed to a dehydrogenase polypeptide under conditions that allow the compound to bind or to otherwise interact with the polypeptide. Soluble dehydrogenase polypeptide is also added to the mixture. If the test compound interacts with the soluble dehydrogenase polypeptide, it decreases the amount of complex formed or activity from the dehydrogenase target. This type of assay is particularly useful in cases in which compounds are sought that interact with specific regions of the dehydrogenase. Thus, the soluble polypeptide that competes with the target dehydrogenase region is designed to contain peptide sequences corresponding to the region of interest.

To perform cell free drug screening assays, it is sometimes desirable to immobilize either the dehydrogenase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/15625 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of dehydrogenase-binding protein found in the bead fraction quantitated from the gel using standard electrophoretic techniques. For example, either the polypeptide or its target molecule can be immobilized utilizing conjugation of biotin and streptavidin with techniques well known in the art. Alternatively, antibodies reactive with the protein but which do not interfere with binding of the protein to its target molecule can be derivatized to the wells of the plate, and the protein trapped in the wells by antibody conjugation. Preparations of a dehydrogenase-binding protein and a candidate compound are incubated in the dehydrogenase-presenting wells and the amount of complex trapped in the well can be quantitated. Methods for detecting such complexes, in addition to those described above for the GST-immobilized complexes, include immunodetection of complexes using antibodies reactive with the dehydrogenase target molecule, or which are reactive with dehydrogenase and compete with the target molecule, as well as enzyme-linked assays which rely on detecting an enzymatic activity associated with the target molecule.

Agents that modulate one of the dehydrogenases of the present invention can be identified using one or more of the above assays, alone or in combination. It is generally preferable to use a cell-based or cell free system first and then confirm activity in an animal/insect model system. Such model systems are well known in the art and can readily be employed in this context.

Modulators of dehydrogenase activity identified according to these drug screening assays can be used to treat a subject with a disorder mediated by the dehydrogenase associated pathway, by treating cells that express the dehydrogenase. The protein of the present invention is expressed in human placenta, as indicated by the library source of the cDNA clone (indicated in FIG. 1). These methods of treatment include the steps of administering the modulators of protein activity in a pharmaceutical composition as described herein, to a subject in need of such treatment.

In yet another aspect of the invention, the dehydrogenases can be used as "bait proteins" in a two-hybrid assay or three-hybrid assay (see, e.g., U.S. Pat. No. 5,283,317; Zervos et al., *Cell* 72:223–232 (1993); Madura et al., *J. Biol. Chem.* 268:12046–12054 (1993); Bartel et al., *Biotechniques* 14:920–924 (1993); Iwabuchi et al., *Oncogene* 8:1693–1696 (1993); and Brent WO94/10300), to identify other proteins that bind to or interact with the dehydrogenase and are involved in dehydrogenase activity. Such dehydrogenase-binding proteins are also likely to be involved in the propagation of signals by the dehydrogenases or dehydrogenase targets as, for example, downstream elements of a dehydrogenase-mediated signaling pathway, e.g., a pain signaling pathway. Alternatively, such dehydrogenase-binding proteins are likely to be dehydrogenase inhibitors.

The two-hybrid system is based on the modular nature of most transcription factors, which consist of separable DNA-binding and activation domains. Briefly, the assay utilizes two different DNA constructs. In one construct, the gene that codes for a dehydrogenase is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a dehydrogenase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the dehydrogenase.

This invention further pertains to novel agents identified by the above-described screening assays. Accordingly, it is within the scope of this invention to further use an agent identified as described herein in an appropriate animal model. For example, an agent identified as described herein (e.g., a dehydrogenase modulating agent, an antisense dehydrogenase nucleic acid molecule, a dehydrogenase-specific antibody, or a dehydrogenase-binding partner) can be used in an animal or insect model to determine the efficacy, toxicity, or side effects of treatment with such an agent. Alternatively, an agent identified as described herein can be used in an animal or insect model to determine the mechanism of action of such an agent. Furthermore, this invention pertains to uses of novel agents identified by the above-described screening assays for treatments as described herein.

The dehydrogenases of the present invention are also useful to provide a target for diagnosing a disease or predisposition to a disease mediated by the peptide, Accordingly, the invention provides methods for detecting the presence, or levels of, the protein (or encoding mRNA) in a cell, tissue, or organism. The protein of the present invention is expressed in human placenta, as indicated by the library source of the cDNA clone (indicated in FIG. 1). The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells, and fluids present within a subject.

The peptides also are useful to provide a target for diagnosing a disease or predisposition to a disease mediated by the peptide, Accordingly, the invention provides methods for detecting the presence, or levels of, the protein in a cell, tissue, or organism. The method involves contacting a biological sample with a compound capable of interacting with the receptor protein such that the interaction can be detected.

The peptides of the present invention also provide targets for diagnosing active disease, or predisposition to a disease, in a patient having a variant peptide. Thus, the peptide can be isolated from a biological sample and assayed for the presence of a genetic mutation that results in translation of an aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations, and immunofluorescence using a detection reagents, such as an antibody or protein binding agent. Alternatively, the peptide can be detected in vivo in a subject by introducing into the subject a labeled anti-peptide antibody. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. The protein of the present invention is expressed in human placenta, as indicated by the library source of the cDNA clone (indicated in FIG. 1). Accordingly, methods for treatment include the use of the dehydrogenase or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the dehydrogenases. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S, or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. The dehydrogenase proteins of the present invention are expressed in human placenta, as indicated by the library source of the cDNA clone (indicated in FIG. 1). Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development. Antibody detection of circulating fragments of the full-length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. The protein of the present invention is expressed in human placenta, as indicated by the library source of the cDNA clone (indicated in FIG. 1). If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. The protein of the present invention is expressed in human placenta, as indicated by the library source of the cDNA clone (indicated in FIG. 1). The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. The protein of the present invention is expressed in human placenta, as indicated by the library source of the cDNA clone (indicated in FIG. 1). Thus, where a specific protein has been correlated with expression in a specific tissue, antibodies that are specific for this protein can be used to identify a tissue type.

The antibodies are also useful for inhibiting protein function, for example, blocking the binding of the dehydrogenase to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use.

Nucleic Acid Molecules

The present invention further provides isolated nucleic acid molecules that encode a dehydrogenase polypeptide of the present invention. Such nucleic acid molecules will consist of, consist essentially of, or comprise a nucleotide sequence that encodes one of the dehydrogenase polypeptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule. The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is:at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

Full-length genes may be cloned from known sequence using any one of a number of methods known in the art. For example, a method which employs XL-PCR (Perkin-Elmer, Foster City, Calif.) to amplify long pieces of DNA may be used. Other methods for obtaining full-length sequences are well known in the art.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the dehydrogenase polypeptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding, and stability of mRNA. In addition, the nucleic acid molecule may be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention and that encode obvious variants of the dehydrogenases of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or whole organisms. Accordingly, as discussed above, the variants can contain nucleotide substitutions, deletions inversions, and/or insertions. Variation can occur in either or both the coding and non-coding regions. The variations can produce both conservative and non-conservative amino acid substitutions.

The present invention further provides non-coding fragments of the nucleic acid molecules provided in the FIGS. 1 and 3. Preferred non-coding fragments include, but are not limited to, promoter sequences, enhancer sequences, gene modulating sequences, and gene termination sequences. Such fragments are useful in controlling heterologous gene expression and in developing screens to identify gene-modulating agents.

A fragment comprises a contiguous nucleotide sequence greater than 12 or more nucleotides. Further, a fragment could be at least 30, 40, 50, 100 250, or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50, or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. The gene encoding the novel dehydrogenase protein of the present invention is located on a genome component that has been mapped to human chromosome 12 (as indicated in FIG. 3), which is supported by multiple lines of evidence, such as STS and BAC map data.

FIG. 3 provides information on SNPs that have been found in a gene encoding the dehydrogenase of the present invention. SNPs were identified at 17 different nucleotide positions. Some of these SNPs, which are located outside the ORF and in introns, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65° C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 17 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as those, which may encompass fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel dehydrogenase protein of the present invention is located on a genome component that has been mapped to human chromosome 12 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides. Moreover, the nucleic acid molecules are useful for constructing transgenic animals wherein a homolog of the nucleic acid molecule has been "knocked-out" of the animal's genome.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form, and distribution of nucleic acid expression. The dehydrogenase proteins of the present invention are expressed in human placenta, as indicated by the library source of the cDNA clone (indicated in FIG. 1). Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in dehydrogenase expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a dehydrogenase, such as by measuring a level of a receptor-encoding nucleic acid in a sample of cells from a subject e.g., mRNA or genomic DNA, or determining if a receptor gene has been mutated. The dehydrogenase proteins of the present invention are expressed in human placenta, as indicated by the library source of the cDNA clone (indicated in FIG. 1).

Nucleic acid expression assays are useful for drug screening to identify compounds that modulate dehydrogenase nucleic acid expression.

The invention thus provides a method for identifying a compound that can be used to treat a disorder associated with nucleic acid expression of the dehydrogenase gene, particularly biological and pathological processes that are mediated by the dehydrogenase in cells and tissues that express it. The protein of the present invention is expressed in human placenta, as indicated by the library source of the cDNA clone (indicated in FIG. 1). The method typically includes assaying the ability of the compound to modulate the expression of the dehydrogenase nucleic acid and thus identifying a compound that can be used to treat a disorder characterized by undesired dehydrogenase nucleic acid expression. The assays can be performed in cell-based and cell-free systems. Cell-based assays include cells naturally expressing the dehydrogenase nucleic acid or recombinant cells genetically engineered to express specific nucleic acid sequences.

The assay for dehydrogenase nucleic acid expression can involve direct assay of nucleic acid levels, such as mRNA levels, or on collateral compounds involved in the signal pathway. Further, the expression of genes that are up- or down-regulated in response to the dehydrogenase signal pathway can also be assayed. In this embodiment the regulatory regions of these genes can be operably linked to a reporter gene such as luciferase.

Thus, modulators of dehydrogenase gene expression can be identified in a method wherein a cell is contacted with a candidate compound and the expression of mRNA determined. The level of expression of dehydrogenase mRNA in the presence of the candidate compound is compared to the level of expression of dehydrogenase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate dehydrogenase nucleic acid expression in cells and tissues that express the dehydrogenase. The dehydrogenase proteins of the present invention are expressed in human placenta, as indicated by the library source of the cDNA clone (indicated in FIG. 1). Modulation includes both up-regulation (i.e. activation or agonization) or down-regulation (suppression or antagonization) of nucleic acid expression.

Alternatively, a modulator for dehydrogenase nucleic acid expression can be a small molecule or drug identified using the screening assays described herein as long as the drug or small molecule inhibits the dehydrogenase nucleic acid expression in the cells and tissues that express the protein. The protein of the present invention is expressed in human placenta, as indicated by the library source of the cDNA clone (indicated in FIG. 1).

The nucleic acid molecules are also useful for monitoring the effectiveness of modulating compounds on the expression or activity of the dehydrogenase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in dehydrogenase nucleic acid, and particularly in qualitative changes that lead to pathology. The nucleic acid molecules can be used to detect mutations in dehydrogenase genes and gene expression products such as mRNA. The nucleic acid molecules can be used as hybridization probes to detect naturally occurring genetic mutations in the dehydrogenase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns, or changes in gene copy number, such as amplification. Detection of a mutated form of the dehydrogenase gene associated with a dysfunction provides a diagnostic tool for an active disease or susceptibility to disease when the disease results from overexpression, underexpression, or altered expression of a dehydrogenase.

Individuals carrying mutations in the dehydrogenase gene can be detected at the nucleic acid level by a variety of techniques. FIG. 3 provides information on SNPs that have been found in a gene encoding the dehydrogenase of the present invention. SNPs were identified at 17 different nucleotide positions. Some of these SNPs, which are located outside the ORF and in introns, may affect control/regulatory elements. The gene encoding the novel dehydrogenase protein of the present invention is located on a genome component that has been mapped to human chromosome 12 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a dehydrogenase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant dehydrogenase gene and a wild-type gene can be determined by direct DNA sequencing. A variety of automated sequencing procedures can be utilized when performing the diagnostic assays (Naeve, C. W., *Biotechniques* 19:448 (1995)), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the dehydrogenase gene in an individual in order to select an appropriate compound or dosage regimen for treatment. FIG. 3 provides information on SNPs that have been found in a gene encoding the dehydrogenase of the present invention. SNPs were identified at 17 different nucleotide positions. Some of these SNPs, which are located outside the ORF and in introns, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control dehydrogenase gene expression in cells, tissues, and organisms. A DNA antisense nucleic acid molecule is designed to be complementary to a region of the gene involved in transcription, preventing transcription and hence production of dehydrogenase. An antisense RNA or DNA nucleic acid molecule would hybridize to the mRNA and thus block translation of mRNA into dehydrogenase.

Alternatively, a class of antisense molecules can be used to inactivate mRNA in order to decrease expression of dehydrogenase nucleic acid. Accordingly, these molecules can treat a disorder characterized by abnormal or undesired dehydrogenase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the dehydrogenase, such as ligand binding.

The nucleic acid molecules also provide vectors for gene therapy in patients containing cells that are aberrant in dehydrogenase gene expression. Thus, recombinant cells, which include the patient's cells that have been engineered ex vivo and returned to the patient, are introduced into an individual where the cells produce the desired dehydrogenase to treat the individual.

The invention also encompasses kits for detecting the presence of a dehydrogenase nucleic acid in a biological sample. The dehydrogenase proteins of the present invention are expressed in human placenta, as indicated by the library source of the cDNA clone (indicated in FIG. 1). For example, the kit can comprise reagents such as a labeled or labelable nucleic acid or agent capable of detecting dehydrogenase nucleic acid in a biological sample; means for determining the amount of dehydrogenase nucleic acid in the sample; and means for comparing the amount of dehydrogenase nucleic acid in the sample with a standard. The compound or agent can be packaged in a suitable container. The kit can further comprise instructions for using the kit to detect dehydrogenase mRNA or DNA.

Nucleic Acid Arrays

The present invention further provides arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides that are only 7–20 nucleotides in length. The microarray may contain oligonucleotides that cover the known 5', or 3', sequence, sequential oligonucleotides that cover the full-length sequence; or unique oligonucleotides selected from particular areas along the length of the sequence. Polynucleotides used in the microarray may be oligonucleotides that are specific to a gene or genes of interest.

In order to produce oligonucleotides to a known sequence for a microarray, the gene(s) of interest (or an ORF identified from the contigs of the present invention) is typically examined using a computer algorithm that starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of one or more of the proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention. FIG. 3 provides information on SNPs that have been found in a gene encoding the dehydrogenase of the present invention. SNPs were identified at 17 different nucleotide positions. Some of these SNPs, which are located outside the ORF and in introns, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the human genome disclosed herein; and (b) one or more other containers comprising one or more of the following: wash reagents, reagents capable of detecting presence of a bound nucleic acid. Preferred kits will include chips that are capable of detecting the expression of 10 or more, 100 or more, or 500 or more, 1000 or more, or all of the genes expressed in Human.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified dehydrogenase genes of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterodehydrogenase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J*. 6:229–234 (1987)), pMFa (Kurjan et al., *Cell* 30:933–943(1982)), pJRY88 (Schultz et al., *Gene* 54:113–123 (1987)), and pYES2 (invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance, propagation, or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a dehydrogenase polypeptide that can be further purified to produce desired amounts of dehydrogenase or fragments. Thus, host cells containing expression vectors are useful for peptide production.

Host cells are also useful for conducting cell-based assays involving the dehydrogenase or dehydrogenase fragments. Thus, a recombinant host cell expressing a native dehydrogenase is useful for assaying compounds that stimulate or inhibit dehydrogenase function.

Host cells are also useful for identifying dehydrogenase mutants in which these functions are affected. If the mutants naturally occur and give rise to a pathology, host cells containing the mutations are useful to assay compounds that have a desired effect on the mutant dehydrogenase (for example, stimulating or inhibiting function) which may not be indicated by their effect on the native dehydrogenase.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a dehydrogenase and identifying and evaluating modulators of dehydrogenase activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the dehydrogenase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the dehydrogenase to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, dehydrogenase activation, and signal transduction, may not be evident from in vitro cell-free or cell-based assays. Accordingly, it is useful to provide non-human transgenic animals to assay in vivo dehydrogenase function, including ligand interaction, the effect of specific mutant dehydrogenases on dehydrogenase function and ligand interaction, and the effect of chimeric dehydrogenases. It is also possible to assess the effect of null mutations, which is mutations that substantially or completely eliminate one or more dehydrogenase functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. An isolated polypeptide having an amino acid sequence consisting of SEQ ID NO:2.
2. An isolated polypeptide having an amino acid sequence comprising SEQ ID NO:2.
3. A composition comprising the polypeptide of claim 1 and a carrier.
4. A composition comprising the polypeptide of claim 2 and a carrier.

* * * * *